US006900185B1

(12) United States Patent
Griffith et al.

(10) Patent No.: US 6,900,185 B1
(45) Date of Patent: May 31, 2005

(54) METHOD OF INDUCING TUMOR CELL APOPTOSIS USING TRAIL/APO-2 LIGAND GENE TRANSFER

(75) Inventors: Thomas S. Griffith, Coralville, IA (US); Timothy Ratliff, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/547,742

(22) Filed: Apr. 12, 2000

(51) Int. Cl.$^7$ .................. A01N 43/04; A01N 63/00; C12N 15/00; C12N 15/63; C07H 21/04

(52) U.S. Cl. .................. 514/44; 435/320.1; 435/455; 424/93.21; 536/23.5; 536/24.1

(58) Field of Search .................. 514/44; 435/320.1, 435/455; 424/93.21, 93.2, 93.1; 536/23.5, 24.1, 23

(56) References Cited

U.S. PATENT DOCUMENTS

| | | | | |
|---|---|---|---|---|
| 5,601,818 A | | 2/1997 | Freeman et al. | .......... 424/93.21 |
| 5,763,223 A | | 6/1998 | Wiley et al. | .............. 435/69.5 |
| 5,763,416 A | * | 6/1998 | Bonadio et al. | .............. 514/44 |
| 5,972,899 A | * | 10/1999 | Zychlinsky et al. | .......... 514/44 |
| 5,994,298 A | | 11/1999 | Tsai et al. | ...................... 514/8 |
| 6,030,945 A | * | 2/2000 | Ashkenazi | .................... 514/12 |

FOREIGN PATENT DOCUMENTS

| | | | | |
|---|---|---|---|---|
| WO | 97/01633 | 1/1997 | ........... | C12N/15/09 |
| WO | 99/12963 | 3/1999 | ........... | C07K/14/00 |

OTHER PUBLICATIONS

Wiley et al., Dec. 1995. Immunity, vol. 3, p. 673–682.*
Bonavida et.al.; Selectively of TRAIL–mediated apoptosos of cancer cells and synergy with drugs: The trail to non–toxic cancer therapeutics, 1999, International Journal of Oncology 15: 793–802.*
Hu et.al.; Development of an Adenovirus Vector with Tetracycline–regulatable Human Tumor Necrosis Factor Gene Expression. 1997. Cancer Research 57 3339–3343.* 2833–2840.*
Pitti et.al.; Induction of Apoptosis by Apo–2 Ligand, a New Member of the Tumor Necrosis Factor Cytokine Family, 1996, JBC, vol. 271: 12687–12690.*
Kaye et.al.; A single amino acid substitution results in a retinoblastoma protein defective in phosphorylation and oncoprotein binding, 1990, Proc. Natl. Acad. sci. vol. 87: 6922–6926.*
Rudinger; Characteristics of the amino acids as components of a peptide hormone sequence, 1976, Peptide Hormones. 1–7.*
Verma et.al.; Gene therapy–promises, problems and prospects, 1997, Nature, vol. 389: 239–242.*
Eck et.al.; Gene–Based Therapy. 1996. Pharmacological Basis of Therapeutics: 77–101.*

Navarro et al., Gene Therapy for Cancer, 1999, Europan Journal of Cancer, vol. 35, No. 6, pp. 867–885.*
Arai et al., Gene transfer of Fas ligand induces tumor regression in vivo, Dec. 1997, Proc. Natl. Acad. Sci., vol. 94, pp. 13862–13867.*
Walczak et al Tumoricidal activity of tumor necrosis factor–related apoptosis–inducing ligand in vivo. Feb. 1999, Nature.*
Gliniak et al., Tumor Necrosis Factor–related Apoptosis–inducing Ligand's Antiumor Activity in Vivo is Enhanced by the Chemotherapeutic Agent CPT–11, Dec. 15, 1999, Cancer Research, vol. 59, pp. 6153–6158.*
Chinnaiyan, A.M., et al., "Combined effect of tumor necrosis factor–related apoptosis–inducing ligand and ionizing radiation in breast cancer therapy", *PNAS, 97* (4), pp. 1754–1759, (Feb. 15, 2000).
Griffith, T.S., et al., "Adenoviral–mediated gene tranfer of TRAIL induces tumor cell apoptosis", *FASEB J., 14* (6), p. A1003, (May 12–16, 2000).
Griffith, T.S., et al., "Adenoviral–Mediated transfer of the TNF–related apoptosis–inducing ligand/Apo–2 ligand gene induces tumor cell apoptosis", *J. of immunology, 165*, pp. 2886–2894, (Sep. 2000).
Putzer, B.M., et al., "Combination therapy with interleukin–2 and wild–type p53 expressed by adenoviral vectors potentiates tumor regression in a murine model of breast cancer", *Human Gene Therapy, 9* (5), pp. 707–718, (Mar. 20, 1998).
Roth, W., et al., "Death ligands/death receptors, new weapons against malignant glioma", *Neuroforum, vol. 5* (3), pp. 87–92, (1999).
Son, K., "Cisplatin–based tumor necrosis factor–related apoptosis–inducing ligand (trail) gene therapy of human breast carcinoma resistant to drugs or hormone", *Breast Cancer Research and Treatment, 57* (1), p. 54, (Dec. 8–11, 1999).
Alderson, M.R., et al., "Fas Ligand Mediates Activation–induced Cell Death in Human T Lymphocytes", *J. Exp. Med., 181*, pp. 71–77, (Jan. 1995).
Armitage, R.J., "Tumor necrosis factor receptor superfamily members and their ligands", *Current Opinion in Immunology, 6*, pp. 407–413, (1994).
Ashkenazi, A., et al., "Safety and antitumor activity of recombinant soluble Apo2 ligand", *The Journal of Clinical Investigation, 104* (2), pp. 155–162, (Jul. 1999).

(Continued)

*Primary Examiner*—Shin-Lin Chen
(74) *Attorney, Agent, or Firm*—Fish & Richardson P.C., P.A.

(57) ABSTRACT

The present invention is directed to methods for inhibiting tumor cell growth, causing tumor regression or eliminating tumor cells in a mammal afflicted with a tumor by administering to a TRAIL-sensitive cell a vector having a DNA expression cassette containing a promoter and a DNA sequence encoding TRAIL, wherein the expression of TRAIL results in tumor inhibition, regression or elimination.

24 Claims, 11 Drawing Sheets

OTHER PUBLICATIONS

Bergelson, J.M., et al., "Isolation of a Common Receptor for Coxsackie B Viruses and Adenoviruses 2 and 5", *Science, 275*, pp. 1320–1323, (Feb. 1997).
Cerami, A., et al., "The role of cachectin/TNF in endotoxic shock and cachexia", *Immunology Today, 9 (1)*, pp. 28–31, (1988).
Cosman, D., "A Family of Ligands for te TNF Receptor Superfamily", *Stem Cells, 12*, pp. 440–455, (1994).
Degli–Esposti, M.A., et al., "Cloning and Characterization of Trail–R3, a Novel Member of the Emerging Trail Receptor Family", *J. Exp. Med., 186 (7)*, pp. 1165–1170, (Oct. 1997).
Degli–Esposti, M.A., et al., "The Novel Receptor TRAIL–R4 Induces NF–kB and Protects against TRAIL–Mediated Apoptosis, yet Retains an Incomplete Death Domain", *Immunity, 7*, pp. 813–820, (Dec. 1997).
Griffith, T.S., et al., "Fas Ligand–Induced Apoptosis as a Mechanism of Immune Privilege", *Science, 270*, pp. 1189–1192, (Nov. 1995).
Griffith, T.S., et al., "Suppression of tumor growth following intralesional therapy with TRAIL recombinant adenovirus", *Moelcular Therapy*, vol. 4, No. 3, 1–10, (Sep. 2001).
Griffith, T.S., et al., "TRAIL: a molecular with multiple receptors and control mechanisms", *Current Opinion in Immunology, 10 (5)*, pp. 559–563, (Oct. 1998).
Hahne, M., et al., "Melanoma Cell Expression of Fas(Apo–1/CD95) Ligand: Implications for Tumor Immune Escape", *Science, 274*, pp. 1363–1366, (Nov. 1996).
Landis, S.H., et al., "Cancer Statistice, 1999", *CA—Cancer Journal for Clinicians, 49 (1)*, pp. 8–31, (Jan./Feb. 1999).
MacFarlane, M., et al., "Identification and Molecular Cloning of Two Novel Receptors for the Cytotoxic Ligand TRAIL", *The Journal of Biological Chemistry, 272 (41)*, pp. 25417–25420, (Oct. 1997).
Marsters, S.A., et al., "A novel receptor for Apo2L/TRAIL contains a truncated death domain", *Current Biology, 7*, pp. 1003–1006, (1997).
Ogasawara, J., et al., "Lethal effect of the anti–Fas antibody in mice", *Nature, 364*, pp. 806–809, (Aug. 1993).
Pan, G., et al., "An Antagonist Decoy Receptor and a Death Domain–Containing Receptor for TRAIL", *Science, 277*, pp. 815–818, (Aug. 1997).
Pan, G., et al., "The Receptor for the Cytotoxic Ligand TRAIL", *Science, 276*, pp. 111–113, (Apr. 1997).
Pan, G., et al., "Trundd, a new member of the TRAIl receptor family that antagonizes TRAIL signalling", *FEBS Letters, 424*, pp. 41–45, (1998).
Pitti, R.M., et al., "Induction of Apoptosis by Apo–2 Ligand, a New Member of the Tumor Necrosis Factor Cytokine Family", *The Journal of Biological Chemistry, 271 (22)*, pp. 12687–12690, (May 1996).
Schneider, P., et al., "Conversion of Membrane–bound Fas(CD95) Ligand to Its Soluble Form is Associated with Downregulation of Its Proapoptotic Activity and Loss of Liver Toxicity", *J. Exp. Med., 187 (8)*, pp. 1205–1213, (Apr. 1998).
Schulze–Osthoff, K., et al., "Apoptosis signaling by death receptors", *Eur. J. Biochem., 254*, pp. 439–459, (1998).
Sheridan, J.P., et al., "Control of TRAIL–Induced Apoptosis by a Family of Signaling and Decoy Receptors", *Science, 277*, pp. 818–821, (Aug. 1997).
Siemens, D.R., et al., "Biomarker distribution after injection into the canine prostate: implications for gene therapy", *BJU International*, vol. 86, No. 9, 1076–1083, (Dec. 2000).
Siemens, D.R., et al., "Cutting edge: Restoration of the ability to generate CTL in mice immune in adenovirus by delivery of virus in a collagen–based matrix", *The Journal of Immunology*, vol. 166, No. 2, 731–735, (Jan. 15, 2001).
Siemens, D.R., et al., "Viral vector delivery in solid–state vehicles: Gene expression in a murine prostate cancer model", *J. National Cancer Inst.*, vol. 92, No. 5, 403–412, (Mar. 1, 2000).
Song, K., et al., "Tumor Necrosis Factor–related Apoptosis–inducing Ligand (TRAIL) Is an Inhibitor of Autoimmune Inflammation and Cell Cycle Progression", *J. Exp. Med., 191 (7)*, pp. 1095–1103, (Apr. 3, 2000).
Steiner, M.S., et al., "Gene therapy for prostate cancer: Where are we now?", *The Journal of Urology*, vol. 164, 1121–1136, (Oct. 2000).
Tomko, R.P., et al., "HCAR and MCAR: The human and mouse cellular receptors for subgroup C adenovirus and group B coxsackieviruses", *PNAS, 94*, pp. 3352–3356, (Apr. 1997).
Wickham, T.J., et al., "Integrins Avbeta3 and avbeta5 Promote Adenovirus Internalization but Not Virus Attachment", *Cell, 73*, pp. 309–319, (Apr. 1993).
Wiley, S.R., et al., "Identification and Characterization of a New Member of the TNF Family that Induces Apoptosis", *Immunity, 3*, pp. 673–683, (Dec. 1995).
Zheng, L., et al., "Induction of apoptosis in mature T cells by tumour necrosis factor", *Nature, 377*, pp. 348–351, (Sep. 1995).
Benedict et al., "Three Adenovirus E3 Proteins Cooperate to Evade Apoptosis by Tumor Necrosis Factor–related Apoptosis–inducing Ligand Receptor–1 and –2," *The Journal of Biological Chemistry*, 2001, 276:3270–3278.
Elsing et al., "The adenovirus E3/10.4K–14.5K proteins down–modulate the apoptosis receptor Fas/Apo–1 by inducing its internalization," *Proc. Natl. Sci. USA*, 1998, 95:10072–10077.
Shisler et al., "The Adenovirus E3–10.4K/14.5K Complex Mediates Loss of Cell Surface Fas (CD95) and Resistance to Fas–Induced Apoptosis," *Journal of Virology*, 1997, 71:8299–8306.
Thomas et al., "TNF–Related Apoptosis–Inducing Ligand (TRAIL) Induces Apoptosis in Fas Ligand–Resistant Melanoma Cells and Mediates CD4 T Cell Killing of Target Cells," *The Journal of Immunology*, 1998, 161:2195–2200.
Tollefson et al., "Forced degradation of Fas inhibits apoptosis in adenovirus–infected cells," *Nature*, 1998, 392:726–730.

\* cited by examiner

A.

B.

Soluble TRAIL

Ad-βgal

Ad-TRAIL

METHOD OF INDUCING TUMOR CELL APOPTOSIS USING TRAIL/APO-2 LIGAND GENE TRANSFER

BACKGROUND OF THE INVENTION

Members of the tumor necrosis factor (TNF) superfamily of cytokines influence a variety of immunological functions, including cellular activation, proliferation, and death, upon interaction with a corresponding superfamily of receptors (1–3). Interest in the apoptosis-inducing molecules TNF and Fas ligand has been peaked due to their participation in events such as autoimmune disorders, activation-induced cell death, immune privilege, and tumor evasion from the immune system (4–8). Another death-inducing family member, TRAIL(TNF-related apoptosis-inducing ligand, also referred to as Apo-2 ligand or Apo-2L) is generating excitement because of its apparent unique ability to induce apoptosis in a wide range of transformed cell lines but not in normal tissues and cells (9,10).

To date, four homologous, but distinct, human TRAIL receptors have been identified, with two [DR4(11; hereafter referred to as TRAIL-R1) and DR5/TRAIL-R2 (12–15)] having the ability to initiate the apoptosis signaling cascade after ligation and two [TRID/DcR1/TRAIL-R3 (12,13,15, 16) and TRAIL-R4/DcR2/TRUNDD (17–19)] lacking this ability. Because they lack the ability to directly signal cell death, TRAIL-R3 and TRAIL-R4 have been hypothesized as being protective receptors, either by acting as "decoy" receptors (11,12,18,19) or via transduction of an anti-apoptotic signal (17).

Given the tumor cell-selectivity of TRAIL's cytotoxicity from results obtained in vitro, recent studies have examined the safety and antitumor activity of recombinant, soluble TRAIL in vivo (20–22). TRAIL was found to be well tolerated when multiple doses were given to normal animals, and no histological or functional changes were observed in any of the tissues or organs examined. These results were hemorrhage, and ultimately death (20,23,24). Moreover, multiple injections of soluble TRAIL into mice beginning the day after tumor implantation significantly suppressed the growth of the tumors, with many animals being tumor-free (20–22).

A major drawback to these findings was that large amounts of soluble TRAIL were required to inhibit tumor formation. This may be due to the pharmacokinetic profile of soluble TRAIL that indicated that after intravenous injection the majority of the protein is cleared within 5 hours (20). Increasing the in vivo half-life of recombinant soluble TRAIL or developing an alternative means of delivery may increase the relative tumoricidal activity of TRAIL such that larger, more establish tumors could be eradicated as efficiently as smaller tumors. The identification of alternate methods to deliver TRAIL to the tumor site, however, is also critical for the further development and testing of the antitumor activity of TRAIL in vivo.

The development of alternate or adjuvant forms of cancer therapy is crucial, due to the increasing rates of many cancers throughout the world. For example, prostate cancer is one of the most prevalent cancers among U.S. males, with annual death rates currently estimated at over 40,000 (61). Current treatment for localized prostate cancer is limited to surgery or radiation therapy, whereas androgen ablation is generally accepted as the best method for treating metastatic prostate cancer. Unfortunately, a significant number of patients with advanced prostate cancer fail to demonstrate any initial positive response to androgen ablation therapy. Moreover, prostatic cells often lose their dependency on androgen during cancer progression, and androgen ablation becomes ineffective, leading to tumor progression and death within 3 years.

With the incidence of cancer and deaths resulting form cancer increasing, there remains a continuing need for the development of alternative therapeutic molecules and treatments for cancer. In particular, there is an on-going need for therapies that have minimal toxic side effects.

SUMMARY OF THE INVENTION

The present invention provides a method for inhibiting tumor cell growth in a mammal afflicted with a tumor comprising administering a vector comprising a DNA expression cassette comprising a promoter and a DNA sequence encoding TRAIL, wherein the expression of TRAIL protein results in tumor inhibition. The vector may be a non-replicative viral vector. The vector may be adenovirus, adeno-associated virus, herpesvirus, lentivirus, retrovirus, vaccinia virus, or other gene delivery vector, or naked DNA. The TRAIL may be human TRAIL. The promoter used in the present invention may be, but is not limited to, a cytomegalovirus promoter, an RSV promoter, or a tissue-specific promoter. The expression cassette may further comprise regulatory elements including, but not limited to, enhancers and tissue-specific regulatory elements regulating TRAIL expression or controlling viral replication. The method of the present invention may also include administering a chemotherapeutic agent, a radiotherapeutic agent, or an immune potentiating gene or protein.

The tumor to be treated using the method of the present invention may be a solid tumor and may be cancerous. In particular, the solid tumor may be a lung tumor, a melanoma, a mesothelioma, a mediastinum tumor, esophagal tumor, stomach tumor, pancreal tumor, renal tumor, liver tumor, hepatobiliary system tumor, small intestine tumor, colon tumor, rectum tumor, anal tumor, kidney tumor, ureter tumor, bladder tumor, prostate tumor, urethral tumor, testicular tumor, gynecological organ tumor, ovarian tumor, breast tumor, endocrine system tumor, or central nervous system tumor.

In the present invention, the vector may be administered by injection. The vector may be administered in combination with a pharmaceutically acceptable carrier. The carrier may be a solution or a slurry, such as Gelfoam* or a matrix. The carrier may further contain an agent that enhances gene delivery and or expression. The carrier may contain immune enhancing agents such as cytokines.

The term "mammal" as used herein refers to any mammal classified as a mammal, including humans, cows, horses, dogs and cats. In particular, the mammal is a human.

The present invention further provides a method for causing tumor regression or elimination in a mammal afflicted with a tumor comprising administering to a TRAIL-sensitive cell a vector comprising DNA encoding TRAIL, wherein the expression of TRAIL protein results in tumor regression or elimination.

The term "inhibition" refers to the halting of the cellular reproduction or growth of a tumor; "regression" refers to the decrease in size of a tumor; and "elimination" refers to the eradication of most or all of the tumor cells. The terms "cancer" and "malignant" are used interchangeably in the present application. "Cancer" or "cancerous" refer to or describe the physiological condition in mammals that is typically characterized by unregulated cell growth. The term "biologically active" for the purposes herein means having the ability to induce or stimulate apoptosis in at least one type of mammalian cell in vivo or ex vivo.

DETAILED DESCRIPTION OF THE INVENTION

Figure 1:
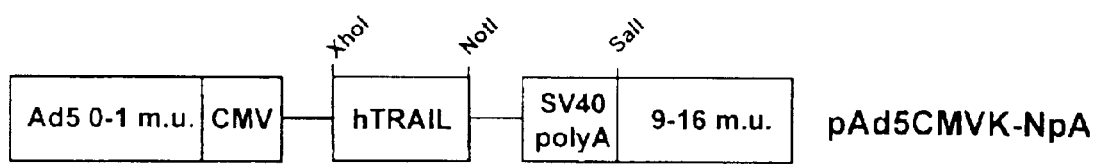
FIG. 1. Generation of adenovirus encoding hTRAIL (Ad5-TRAIL). (A). Map of the vector used to generate Ad5-TRAIL. Map units (m.u.) 2–8, which contains the E1 genes, were deleted from the adenoviral backbone. The hTRAIL cDNA was positioned into the vector behind the immediate early CMV promotor, and in front of the SV40 polyadenylation sequence. Transfection of this vector into human embryonic kidney 293 cells was performed for viral propagation. (B). Ad5-TRAIL-infected 293 cells express TRAIL protein. Cell lysates from uninfected or Ad5-TRAIL-infected 293 cells were prepared 24 hours after infection, and TRAIL protein production was determined by Western blot analysis. Molecular weights listed are in kD.
Figure 1:
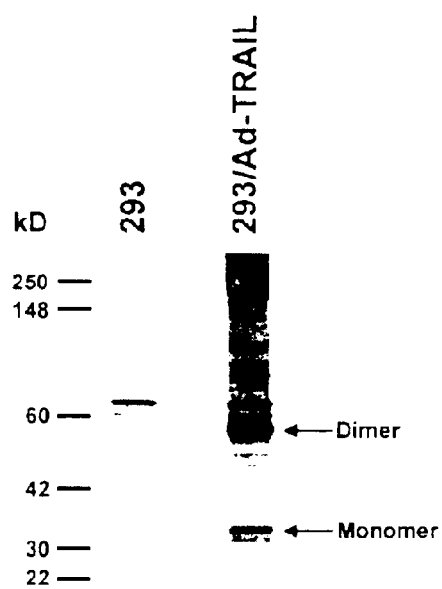

Cell death by necrosis is a pathologic form of cell death resulting from some trauma or cellular injury and is characterized by swelling of the cell, disintegration of the cell membrane and nuclear flocculation. Cell death by apoptosis occurs naturally in many physiological processes, including embryonic development and formation and condensation of chromatin. Decreased levels of apoptotic cell death have been associated with a variety of pathological conditions including cancer, lupus, and herpes virus infection. The present invention is based on the finding that when a vector expressing a nucleic acid expression cassette encoding TRAIL was introduced into a TRAIL-sensitive tumor cell, TRAIL protein was produced, which rapidly led to cell death by apoptosis.

The identification of TRAIL several years ago generated a great deal of interest, when it was determined that it appeared to have the ability to induce apoptosis in a variety of tumor cell lines but not in normal cells in vitro. Moreover, it was observed that TRAIL mRNA is constitutively expressed in a wide variety of cells and tissues. These were unusual characteristics for a death-inducing molecule in the TNF family, as the expression of TNF, LT-α, and Fas ligand is tightly regulated since they can have toxic effects on normal tissues. The tumor-specific activity of TRAIL was extended in vivo with the observation that treatment of SCID and nude mice bearing human tumors with soluble TRAIL significantly inhibited tumor outgrowth without any observable toxic side effects to the host (20–22). This inhibition of tumor outgrowth, though, required high amounts of TRAIL given over several days shortly after tumor implantation. Pharmacokinetic analysis revealed that soluble TRAIL given to mice intravenously displayed an elimination half-life of just under 5 hours (20). Given that many normal tissues express mRNA for at least one of the four TRAIL receptors, this suggests that almost all the tissues in the body have the potential to bind and sequester soluble TRAIL and, thus, prevent it from reaching the tumor.

An alternative approach would be to administer TRAIL locally, where it would exist at a greater concentration and have a better chance of significantly inducing tumor cell death. Such localized, intratumoral injections of soluble TRAIL would, however, be limited in that only a relatively small volume could be administered, suggesting that a potentially suboptimal amount of TRAIL protein would vectors carrying the TRAIL gene. The use of the CMV promoter to drive the transcription of the transferred TRAIL gene serves as an additional mechanism to further increase the local concentration of TRAIL protein because it is not transcriptionally regulated in the same manner as the TRAIL promoter. Only when the process of apoptosis has disrupted cellular functions sufficiently to affect protein production in the Ad-TRAIL-infected tumor cell will the generation of TRAIL stop. In addition to the direct elimination of tumors by the induction of apoptosis, TRAIL-induced apoptotic bodies can function to enhance tumor-specific immune activation. Immune activation may be potentiated by co-delivery of immune activation agents such as cytokines or genes coding for these agents. The concept of gene therapy has recently developed into a viable method of treating malignant transformation and cancer progression. Whereas some therapies have focused on replacing absent critical functional genes in the target cells to restore a normal phenotype, other approaches have been based on introducing genes that encode immunostimulatory molecules to activate the immune system against the tumor. Many of these studies have employed the use of replication-deficient adenoviral vectors derived from adenovirus type 5 (Ad5) to transfer the gene of interest into the target tumor cells. For example, adenoviral vectors encoding CD80, IFN-β, IL-2, IL-7, and IL-12 have all demonstrated the ability to stimulate antitumor responses after administration (41–46). The combination of adenovirus-mediated delivery of the herpes simplex virus thymidine kinase gene and ganciclovir therapy has proved efficacious in treating prostate cancer (47,48). Also, adenoviral vectors expressing Fas ligand have been tested in the treatment of prostate cancer models, experimental glioma, and renal carcinoma (49–51).

Even with these promising observations, immunogenicity remains a potential problem with adenoviral-based vectors. Antibodies present in the patient may quickly neutralize the adenovirus before it can deliver its genetic load, as there is widespread immunity to a variety of adenovirus serotypes in humans. Recent expression even in the presence of pre-existing immunity to adenovirus (43). Intratumoral administration of Ad5-TRAIL provides the virus with an appropriate environment for infection of the tumor and surrounding tissue, which leads to gene expression and sufficient TRAIL protein production to induce tumor cell death.

It was surprising that there were differences in tumor cell death following Ad5-TRAIL infection as compared to soluble TRAIL-induced death. The relative activity of Ad5-TRAIL is dependent upon its ability to infect a target cell. Adenovirus infection requires the expression of CAR (coxsackievirus and adenovirus receptor) and the expression of certain integrins, such as $\alpha_v\beta_3$ and $\alpha_v\beta_5$ (31–33). All of the tumor cell lines and the normal prostate epithelial cells were highly susceptible to adenovirus infection, suggesting that each cell type differentially regulated the translation of TRAIL mRNA into protein. Additional regulation may result in the transport of any TRAIL that is produced from the cytoplasm to the cell surface at different rates. The surface expression of TRAIL is required for apoptosis induction as the inhibition of protein transport by Brefeldin A inhibited cell death, but not the production of TRAIL protein, following Ad5-TRAIL infection.

Whereas surface expression of TRAIL is essential for the observed tumoricidal activity of Ad5-TRAIL, the sensitivity of the cell to TRAIL-induced apoptosis is also an important component of this phenomenon. This was best demonstrated by the fact that the melanoma cell line WM 164 and the normal prostate epithelial cells, which were resistant to soluble TRAIL-mediated apoptosis, were also resistant to effects of Ad5-TRAIL infection. The identification of two TRAIL receptors that are capable of initiating the apoptotic machinery (TRAIL-R1 and-R2) and two that are not (TRAIL-R3 and -R4), led to the initial hypothesis that the expression of TRAIL-R3 and/or -R4 conferred resistance to TRAIL-induced death (11,12,18,19). However, this hypothesis was formulated by examining TRAIL receptor mRNA expression in several normal tissues and tumor cell lines, yet were sensitive to TRAIL (soluble or Ad5-TRAIL-derived) mediated death (36,52) so it is unlikely that expression of either TRAIL-R3 or -R4 plays a role in determining their resistance to TRAIL.

One possible explanation for the resistance of the WM 164 cells to Ad5-TRAIL may come from a component of the cell death machinery called FLIP (FLICE inhibitory protein). FLIP is believed to inhibit the death receptor signaling machinery at its most proximal point by preventing the interaction of caspase-8 and/or FADD to the death domains of cross-linked death receptors, and thus inhibit any downstream apoptotic signaling events (53). Intracellular levels of FLIP are high in the TRAIL-resistant melanoma cell line WM 164 (36), and high FLIP levels have also been shown to correlate with resistance to TRAIL-mediated apoptosis in primary versus transformed keratinocytes (54). While FLIP may have a protective function in the WM 164 tumor cell line, it is likely to be one of several intracellular proteins that cooperate with other molecules (both intracellular and at the cell surface) to regulate TRAIL-induced death in tumor cell lines.

The participation of TRAIL-R3 and-R4 in regulating TRAIL sensitivity may be greater, however, in normal cells/tissues or primary tumors than in established tumor cell lines. The treatment of normal human umbilical vein or microvascular endothelial cells with phospholipase C (to strip the GPI-linked TRAIL-R3 from the surface) and cycloheximide (to prevent the re-expression of any TRAIL-R3) sensitized these cells to TRAIL (13). This would suggest that TRAIL-R3 is a key regulator of the sensitivity of normal cells to TRAIL-induced death, but the addition of cycloheximide may inhibit the production of some other protein (perhaps FLIP) critical for TRAIL resistance. Furthermore, it is not known how much TRAIL-R3 or -R4 is needed to inhibit the formation of a competent TRAIL-R1 or -R2 signaling complex. RT-PCR analysis of the normal prostate epithelial cells detected mRNA species for all four TRAIL receptors (TG, unpublished observation), making it possible for TRAIL-R3 and/or -R4 to enter into the TRAIL-determine at this time what is the exact mechanism that regulates TRAIL sensitivity and resistance in normal cells and tissues.

The observed "suicide"-like death of the Ad5-TRAIL-infected tumor cells is not the only mechanism by which tumor cells may die with this kind of gene transfer therapy in vivo. The intralesional injection of Ad5-TRAIL would likely result in the infection of both cancerous and normal cells surrounding the injection site. While the normal prostate epithelial cells tested in the report were not killed when infected with Ad5-TRAIL, they still produced TRAIL protein from the transferred gene as evidenced by the fact that they could then be used to kill PC-3 cells in a TRAIL-dependent manner (FIGS. 6C & D). This suggests that it would not be imperative for Ad5-TRAIL to infect the tumor cell, as infection in either the tumor itself or the surrounding normal tissue would lead to the localized production of TRAIL. In addition, the apoptotic death resulting from Ad5-TRAIL infection may help initiate a T cell-mediated immune response against any remaining tumor cells. Recent reports have demonstrated that immature dendritic cells (DCs) can engulf apoptotic bodies and present antigens derived from these cell fragments in an MHC class I-restricted fashion upon maturation, resulting the CTL activity (55,56). Likewise, the combination of Ad5-TRAIL with an immunostimulatory cytokine (i.e. IL-12, IFN-γ) may result in the initiation of a tumor-specific immune response against any remaining tumor cells.

The present invention is directed to a gene delivery vehicle, such as a adenoviral vector, engineered to carry a nucleic acid expression cassette encoding TRAIL. The vector carrying the TRAIL gene is injected into the tumor. Shortly after introduction of the vector into TRAIL-sensitive tumor cell targets, TRAIL protein is produced and rapidly leads to the induction of apoptosis in the tumor cells.

This method of administering a vector engineered to encode the nucleic acid for TRAIL is useful in the field of oncology for treating solid mammalian tumors, such as cancers of the lung, melanoma, mesothelioma, mediastinum, esophagus, ovarian, breast, endocrine system, and central nervous system. Those with skill in the art will recognize other possible solid tumor candidates.

The use of a vector containing the TRAIL gene, as opposed to soluble TRAIL protein, allows for a localized expression of TRAIL protein directly in the tumor, resulting in high local TRAIL concentration. In addition, TRAIL protein production is extended over time, therefore diminishing the problems associated with rapid clearance of soluble TRAIL administered systemically.

The TRAIL encoded by DNA of the present invention includes human TRAIL (TRAIL) as well as homologous TRAIL from other mammalian species, TRAIL variants (both naturally occurring variants and those generated by recombinant DNA technology), and TRAIL fragments, i.e., only a portion of the full-length protein, that retain a desired biological activity. The term "biologically active" means having the ability to induce or stimulate apoptosis in at least one type of mammalian cell in vivo or ex vivo. Examples of TRAIL encoded by the DNA of the present invention include nucleotide sequences encoding for TRAIL containing the entire extracellular domain. Fragments of the extracellular domain that retain a desired biological activity are also provided. Such fragments advantageously include regions of TRAIL that are conserved in proteins of the TNF family of ligands. Additional examples of TRAIL polypeptides are those lacking not only the cytoplasmic domain and transmembrane region, but also all or part of the spacer region.

Due to the degeneracy of the genetic code, two DNA sequences may differ, yet encode the same amino acid sequence. The present invention thus provides isolated DNA sequences encoding biologically active TRAIL, selected from DNA comprising the coding region of a native human or mammalian TRAIL cDNA, or fragments thereof, and DNA which is degenerate as a result of the genetic code to the native TRAIL DNA sequence.

A "variant" of TRAIL is a polypeptide that is not completely identical to amino acid sequence of the protein is modified, for example by substitution, to create a polypeptide having substantially the same or improved qualities as compared to the native polypeptide. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall peptide retains its spacial conformation but has altered biological activity. For example, common conserved changes might be Asp to Glu, Asn or Gln; His to Lys, Arg or Phe; Asn to Gln, Asp or Glu and Ser to Cys, Thr or Gly. Alanine is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cystine, tyrosine, asparagine and glutamine having uncharged polar side chains; aspartate and glutamate having acidic side chains; and lysine, arginine, and histidine having basic side chains. L. Stryer, *Biochemistry* (2d ed.) p. 14–15; Lehninger, Biochemistry, p. 73–75.

The amino acid changes are achieved by changing the codons of the corresponding nucleic acid sequence. It is known that such polypeptides can be obtained based on substituting certain amino acids for other amino acids in the polypeptide structure in order to modify or improve biologic activity, such as antigenic or immunogenic activity. For example, through substitution of alternative amino acids, small conformational changes may be conferred upon a polypeptide which result in increased activity. Alternatively, amino acid substitutions in certain polypeptides may be used to provide residues which may then be linked to other molecules to provide peptide-molecule conjugates which retain sufficient biologic properties of homology (percent identity) between a native and a variant sequence may be determined, for example, by comparing the two sequences using computer programs commonly employed for this purpose. One suitable program is the GAP computer program described by Devereux et al. (*Nucl. Acids Res.* 12:387, 1984), which is available from the University of Wisconsin Genetics Computer Group.

The amino acid sequence of the variant TRAIL polypeptide corresponds essentially to the native TRAIL amino acid sequence. As used herein "corresponds essentially to" refers to a polypeptide sequence that will elicit a biological response substantially the same as the response generated by native TRAIL. Such a response may be at least 60% of the level generated by native TRAIL, and may even be at least 80% of the level generated by native TRAIL. A variant of the invention may include amino acid residues not present in the corresponding native TRAIL or deletions relative to the corresponding native TRAIL.

Nucleic acid is "operably linked" when it is placed into a functional relationship with another nucleic acid sequences. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Further, fusion proteins can be generated comprising operably linking multiple copies of the nucleic acid encoding TRAIL or heterologous DNA encoding one or more different proteins into the expression vector. These multiple nucleic Expression vectors that may be used in the present invention are any vehicles capable of delivering the TRAIL gene, such as adenovirus, adeno-associated virus, herpesvirus, lentivirus, retroviruses, vaccinia, or naked DNA. In particular, the expression vector is a non-replicative adenovirus vector. The nucleic acid encoding TRAIL is operably linked to a promoter. The expression vector contains an expression cassette, which is a nucleic acid segment comprising at least a first gene that one desires to have expressed and the necessary regulatory elements for expressing the gene in the target cell. Preferred regulatory elements for use with the invention include promoters, enhancers and terminators.

Most endogenous genes have regions of DNA that are known as promoters, which regulate gene expression. Promoter regions are typically found in the flanking DNA upstream from the coding sequence in both prokaryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous DNAs, that is a DNA different from the native or homologous DNA.

Promoter sequences are also known to be strong or weak, or inducible. A strong promoter provides for a high level of gene expression, whereas a weak promoter provides for a very low level of gene expression. An inducible promoter is a promoter that provides for the turning on and off of gene expression in response to an exogenously added agent, or to an environmental or developmental stimulus. Promoters can also provide for tissue specific or developmental regulation.

The expression cassette of the invention is operably linked to a promoter, which provides for expression of a linked DNA sequence. The DNA sequence is operably linked to the promoter when it is located downstream from the promoter, to form an expression cassette. An isolated promoter sequence that is a strong limited to, a strong mammalian promoter such as the cytomegalovirus promoter, the RSV promoter or any tissue-specific promoter.

The carrier for the TRAIL may be a fluid-based carrier, such as a saline solution, a slurry, such as a gelatin-based carrier, a matrix, collagens or polymers useful to enhance gene transfer or gene expression. For example, the carrier may be Gelfoam*. The carrier may comprise additional compounds that can stimulate or enhance the immune system, such as a cytokine. Alternatively, the carrier may comprise one or more chemotherapeutic agents, radiotherapeutic agents, or immune potentiating genes or proteins. Such therapeutics effective against cancer are well known in the art.

According to the invention, cancer cells are treated in vivo by administration to a mammal afflicted with cancer of an effective amount of the vector containing the TRAIL gene. As used herein, an "effective amount" is that amount that results in an inhibition of growth of the target cancer cells. As described herein, a suitable dose is the vector level capable of inducing a biologically relevant effect.

It will be appreciated that the amount of the compound, derivative thereof, required for use in treatment will vary not only with the particular solution selected but also with the nature of the condition being treated, and the age and condition of the patient. The amount will be ultimately at the discretion of the attendant physician or clinician.

The composition of the present invention can be administered in conjunction with known anti-tumor chemotherapies and/or with known radiation therapies, and/or with known immune potentiating therapies.

The therapeutics described herein are believed to be effective in the treatment of solid mammalian tumors. These solid tumors include lung tumors, melanoma, mesothelioma, mediastinum tumors, esophagal tumors, stomach tumors, pancreal tumors, renal tumors, liver tumors, hepatobiliary system tumors, small intestine tumors, colon tumors, rectum tumors, anal tumors, kidney tumors, ureter gynecological organ tumors, ovarian tumors, breast tumors, endocrine system tumors, or central nervous system tumors.

In the present invention, the entire coding sequence of human TRAIL was cloned into the XhoI and NotI sties of pAd5CMVK-NpA (FIG. 1A). The resultant plasmid and adenovirus backbone sequences restricted of E1 were transfected into human embryonic kidney (HEK) 293 cells, and plaques were isolated and amplified for analysis of TRAIL expression.

Expression of the TRAIL protein results in its interaction with a death-inducing TRAIL-receptor, whereby the cell is induced to die by apoptosis. The TRAIL/TRAIL receptor interaction takes place in the same cell or between adjacent cells. Only the TRAIL-sensitive tumor cells die in this procedure, whereas the surrounding normal tissue is not harmed. Addition of Brefeldin A, a fungal metabolite that specifically blocks protein transport from the endoplasmic reticulum to the Golgi apparatus (and ultimately the cell surface), to the target cells inhibited TRAIL surface expression and subsequent apoptotic death.

The localized production of a membrane-bound form of TRAIL, instead of a soluble form, results in a high "local" concentration of TRAIL that is able to significantly influence tumor cell growth before elimination. This is the first use of TRAIL in a gene transfer/gene therapy setting, which presents a variety of new possibilities for using TRAIL (the gene and/or the protein) as an antitumor agent.

The following examples are intended to illustrate but not limit the invention.

EXAMPLES

Example 1

Production of TRAIL-encoding Adenovirus

The cDNA encoding human TRAIL (hTRAIL) was inserted into the E1 region of a replication deficient adenovirus type 5 construct under the control of the CMV immediate early promoter (FIG. 1A) to form an Ad-TRAIL vector. The cDNA for hTRAIL was obtained from Dr. Hideo Yagita (Juntendo University, generated using standard methods by the University of Iowa Gene Transfer Vector Core (Iowa City, Iowa) (26). Briefly, the entire coding sequence of human TRAIL was cloned into the XhoI and NotI sites of pAd5CMVK-NpA. The resultant plasmid and adenovirus backbone sequences (adenovirus type 5; Ref. 27) that had the E1 (E1A and E1B) genes deleted were transfected into human embryonic kidney (HEK) 293 cells, and viral particles were isolated and amplified for analysis of TRAIL expression. Recombinant adenoviruses encoding nuclear-targeted bacterial β-galactosidase(Ad5-βgal) or green fluorescent protein (Ad5-GFP) were used as virus controls. Recombinant adenoviruses were screened for replication competent virus by A549 plaque assay, and virus titer was determined by plaque assay on 293 cells. Purified viruses were stored in PBS with 3% sucrose and kept at −80° C. until use.

The Ad-TRAIL plasmid was transfected into HEK 293 cells to propagate the virus. Cells were cultured in complete medium, and permitted to adhere for at least 6 hours before adding adenovirus. Prior to infection, cells were washed with PBS, and then the vectors were added at the indicated number of plaque forming units (pfu)/cell in culture medium supplemented as described above but with only 2% FBS. After 4 hours, cells were washed with PBS and incubated in complete medium for the remainder of the assay.

Ad5-TRAIL-infected 293 or uninfected 293 cells were lysed, and the cellular proteins were separated by nonreducing SDS-PAGE to assay for TRAIL expression by Western blotting. Cells were lysed in PBS containing 1% Nonidet P-40, 0.35 mg/ml PMSF, 9.5 µg/ml Leupeptin, and 13.7 µg/ml Pepstatin A. The lysed cells were centrifuged at 14,000×g to remove cellular debris, and protein concentrations of the lysates were determined by the colorimetric bicinchoninic acid analysis (Pierce Chemical Company, Rockford, Ill.). Equal amounts of protein were separated by SDS-PAGE, transferred to nitrocellulose membrane (Novex, San Diego, Calif.), and blocked with 5% nonfat dry milk in PBS-Tween 20 (0.05% v/v) washing, the membrane was incubated with an anti-mouse or anti-rabbit-HRPO antibody (diluted 1:1000, Amersham, Arlington Heights, Ill.) for 1 hours. Antibodies against caspase-8 (provided by Dr. Marcus Peter, University of Chicago), poly (ADP-ribose) polymerase (PARP; Pharmingen, San Diego, Calif.), and hTRAIL (PeproTech, Rocky Hill, N.J.) were used for Western blotting according to manufacturer's instruction. Following several washes, the blots were developed by chemiluminescence according to the manufacturer's protocol (Renaissance chemiluminescence reagent, DuPont NEN, Boston, Mass.).

Amino acid sequence analysis of the TRAIL cDNA predicts a weight of 32.5 kD for TRAIL monomers (9,10). As demonstrated in FIG. 1B, prominent bands migrating at 32–35 kD and 55–58 kD are clearly evident, which correspond to TRAIL monomers and dimers, respectively. Higher order multimers may be present, but were difficult to clearly resolve. In contrast, no corresponding bands were present in the uninfected 293 cell lysate. Thus, these results demonstrate that the adenoviral-mediated gene transfer of hTRAIL results in transgene expression in human cells.

Example 2

Human Tumor Cells are Susceptible to Adenovirus Infection

One of the advantages of using an adenoviral vector lies in the ability to infect epithelial cell populations. Group C adenovirus, such as Ad5, requires the interaction between the viral fiber capsid protein to the coxsackievirus and adenovirus receptor, or CAR, and the viral penton base binding to certain integrins (e.g. α, β, and α,β,) for entry into the cell by receptor-mediated endocytosis (31–33). Therefore, a panel of human tumor cell lines (MDA 231, mammary adenocarcinoma; PC-3, prostate carcinoma; RT-4, bladder papilloma; WM 164, melanoma; and WM 793, melanoma) were tested to verify that they would be receptive to adenoviral infection prior to examining the effects of Ad5-TRAIL infection. lines (WM 164 and WM 793) were obtained from Dr. Meenhard Herlyn (Wistar Institute, Philadelphia, Pa.). The human mammary adenocarcinoma cell line (MDA 231) was obtained from Dr. David Lynch (Immunex Corporation, Seattle, Wash.). The human bladder cancer cell line (RT-4) was obtained from Dr. Scott Crist (University of Iowa, Iowa City, Iowa). PC-3, RT-4, WM 164, and WM 793 were cultured in Dulbecco's modified Eagle's medium (DMEM) supplemented with 10% fetal bovine serum, penicillin, streptomycin, sodium pyruvate, non-essential amino acids, and HEPES (hereafter referred to as complete DMEM). MDA 231 was cultured in RPMI 1640 supplemented with 10% fetal bovine serum, penicillin, streptomycin, sodium pyruvate, non-essential amino acids, and HEPES (hereafter referred to as complete RPMI). Normal human prostate epithelial cells were obtained from Clonetics Corporation (San Diego, Calif.) and cultured as directed.

The tumor cells were infected with either an adenovirus carrying the enhanced green fluorescent protein gene (Ad5-GFP) or the β-galactosidase gene (Ad5-βgal) for 4 hours, and then analyzed 20 hours later to determine adenoviral infection efficiency and transferred gene expression. Cells infected with Ad5-GFP were analyzed by flow cytometry on a FACScan (Becton Dickinson, San Jose, Calif.) at various time points after infection to determine infection efficiency. Cells infected with Ad5-βgal were assayed for β-galactosidase activity with the Galacto-Light Plus chemiluminescent reporter gene assay system (Tropix, Bedford, Mass.) to determine the level of transferred gene expression.

Figure 2A:
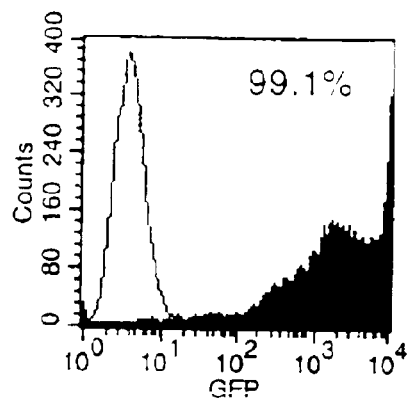
FIG. 2. Susceptibility of human tumor cell lines and normal prostate (1000 pfu/cell for 4 hours) as described in Example 2 below. Infection efficiency was determined after 24 hours incubation by flow cytometry, and open histograms represent uninfected cells and filled histograms represent Ad5-GFP-infected cells. The percentage of GFP-positive cells is indicated for each cell type. All histograms represent $10^4$ gated cells, and viability was >95% as assessed by propidium iodide exclusion. (B). 96-well plates were seeded with $10^4$ cells/well and allowed to attached for at least 6 hours before infection with Ad5-βgal at the indicated number of pfu/cell for 4 hours. β-galactosidase activity was determined after 24 hours incubation using a chemiluminescent reporter gene assay system as described in Example 2 below. Experiments reported in (A) and (B) were repeated at least three times with similar results.
Figure 2A:
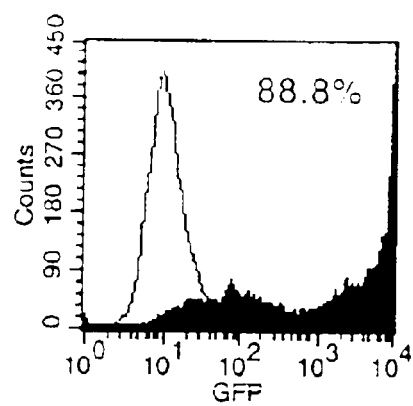
Figure 2A:
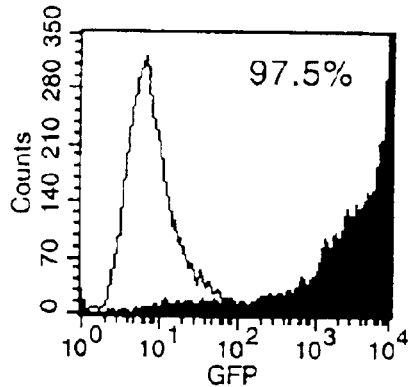
Figure 2A:
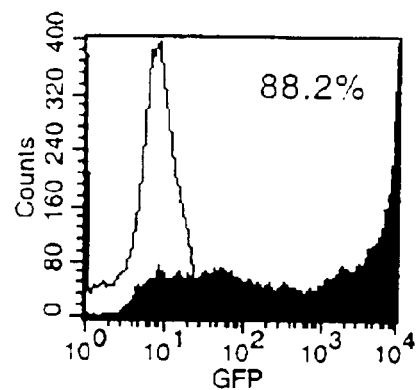
Figure 2A:
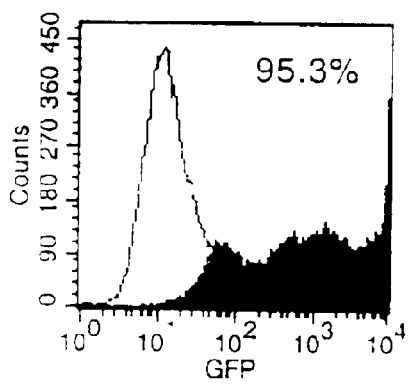
Figure 2A:
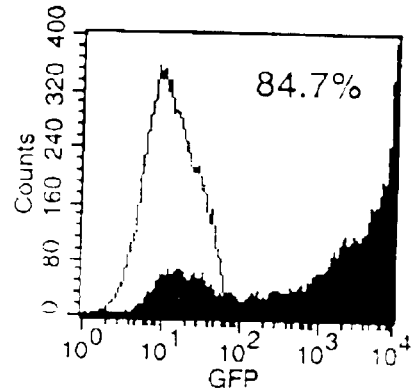
Figure 2:
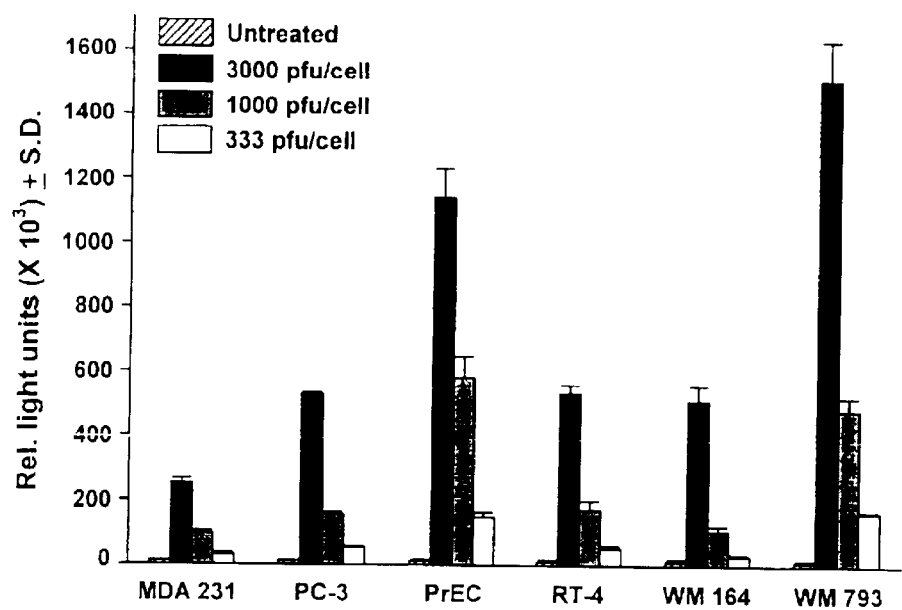

When infected with 1000 pfu/cell Ad5-GFP all of the tumor cell lines demonstrated a high percentage of infectivity, ranging from 84.7–99.1% as measured by flow cytometry (FIG. 2A). Surface expression of TRAIL was determined by measuring the binding of the anti-hTRAIL mAb M181 (mouse IgG1; Immunex). Briefly, cells were incubated with 10 μg/ml M181 or MOPC-21 (nonspecific mouse IgG1 isotype control, Sigma) in 3% BSA in PBS (PBSA) for 30 minutes on ice. Following 3 washes with PBS, cells were incubated with a PE-conjugated, Fc-Grove, Pa.) for 30 minutes on ice. Finally, after 3 washes in PBS, the cells were analyzed on a FACscan (Becton Dickinson).

In addition, normal prostate epithelial cells (PrEC) were also found to be highly susceptible to Ad5-GFP infection (95.3%). Infection with Ad5-βgal revealed that all of the cell types produced protein from the transferred gene in a pfu/cell dependent manner; however, there were greater differences in β-galactosidase activity between the different cell types than seen when examining GFP production (FIG. 2B). Thus, these results indicate that adenoviral-mediated transfer of the β-galactosidase and GFP reporter genes into the cells of interest resulted in efficient gene transcription and translation into protein, suggesting that infection with Ad5-TRAIL should produce TRAIL protein in a similar percentage of cells.

Example 3

Production of TRAIL Following Ad5-TRAIL Infection Leads to Tumor Cell Death

With the demonstration that the human tumor cell line panel was adequately infected with adenovirus, subsequent experiments were performed to examine the consequences of Ad5-TRAIL infection. Tumor cell sensitivity to Ad5-βgal, Ad5-GFP, or Ad5-TRAIL was assayed using the following procedure. Cells were added to 96-well plates ($2\times10^4$ cells/well) in complete medium, and then allowed to adhere for at least 6 hours before infection with the various adenoviral vectors as described above. As a positive control, recombinant soluble hTRAIL was added to the target cells at the indicated concentrations. In some experiments, z-VAD-fmk (20 μM), TRAIL-R2:Fc (20 μg/ml, Immunex), Fas:Fc (20 μg/ml, Pharmingen) or Brefeldin A (5 μg/ml) was added to the medium during and after infection for the remainder of the assay. The peptide caspase inhibitor, z-VAD-fmk was obtained from Enzyme Systems Products (Livermore, Calif.). A stock solution of the inhibitor was prepared in DMSO and stored at 4 C. Brefeldin A was purchased from Epicentre Technologies (Madison, Wis.), with a stock solution prepared in 100% (O.D. cells treated per O.D. cells not treated)] X 100. For analysis of apoptosis, tumor cell targets were incubated as described above and apoptotic cell death was measured by flow cytometry using FITC-conjugated annexin V (R&D Systems, Minneapolis, Minn.) and propidium iodide (Sigma, St. Louis, Mo.) as described (29,30).

Figure 3A:
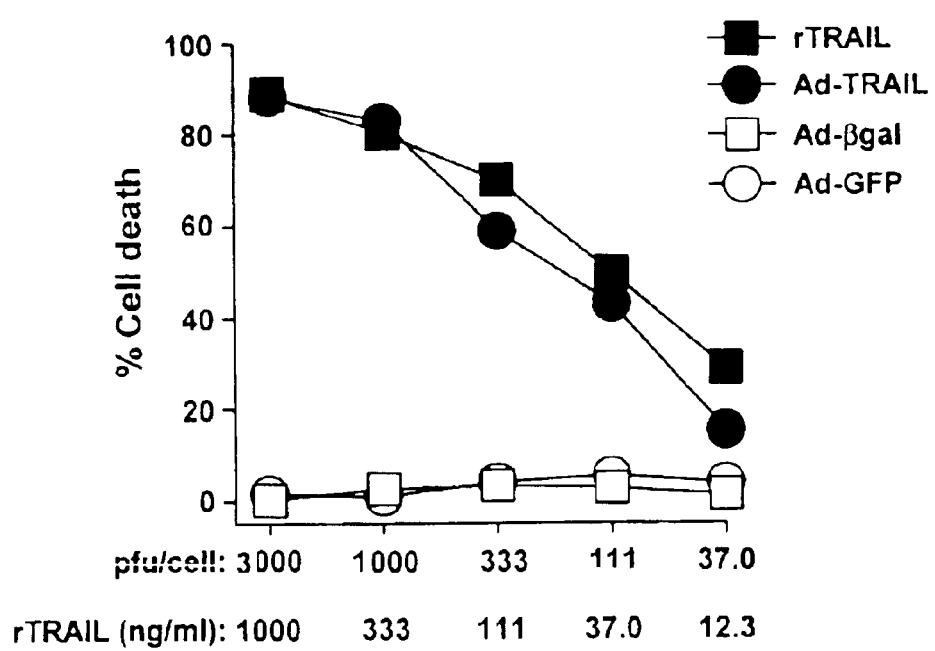
FIG. 3. Death of PC-3 cells after Ad5-TRAIL infection results from increased production of TRAIL protein. (A). Microtiter plates were seeded with $2 \times 10^4$ cells/well and allowed to adhere for at least 6 hours before infection with Ad5-TRAIL, Ad5-βgal, or Ad5-GFP at the indicated number of pfu/cell for 4 hours. Cells were washed with PBS, and then incubated with medium alone or medium containing recombinant TRAIL (TRAIL) at the indicated concentrations. Cell viability was determined after 20 hours by crystal violet staining. Each value represents the mean of three wells. For clarity, S.D. bars were omitted, but were <5% for all data points. Similar results were observed in three independent experiments. (B). Production of TRAIL protein following Ad5-TRAIL infection. 24-well plates containing $5 \times 10^5$ cells/well were infected with Ad5-TRAIL or Ad5-βgal (1000 pfu/cell) for 4 hours, cell lysates were prepared at the indicated times after infection, and TRAIL protein levels were determined by Western blot analysis. Lysates of uninfected PC-3 cells or Ad5-TRAIL-infected 293 cells were used as negative and positive controls, respectively.

The tumor cells were infected with either Ad5-βgal or Ad5-TRAIL for 4 hours, and then cultured for an additional 20 hours before determining the amount of cell death. As indicated in FIG. 3A, minimal cell death of PC-3 cells was observed upon infection with Ad5-βgal. In contrast, a significant increase in cell death was seen with Ad5-TRAIL infection. Moreover, the level of cell death induced by Ad5-TRAIL infection was comparable to that of soluble TRAIL-induced death. This cytotoxic activity was seen with other TRAIL-sensitive tumor cell targets, but not with the TRAIL-resistant melanoma cell line WM 164 or normal prostate epithelial cells (PrEC) (Table I).

TABLE I

Tumoricidal activity of adenovirus vectors versus TRAIL.

| Target cell | Ad5-βgal[1] | Ad5-TRAIL[1] | TRAIL[2] |
|---|---|---|---|
| MDA 231 (breast) | 2.4 ± 1.4 | 44.7 ± 5.6 | 89.9 ± 0.9 |
| PC-3 (prostate) | 1.4 ± 1.8 | 85.5 ± 5.2 | 90.1 ± 8.7 |
| RT4 (bladder) | 1.3 ± 1.0 | 82.4 ± 6.1 | 89.4 ± 5.0 |
| WM 164 (melanoma) | 3.8 ± 2.1 | 1.2 ± 0.8 | 5.2 ± 2.7 |
| WM 793 (melanoma) | 2.5 ± 2.8 | 56.7 ± 9.7 | 86.6 ± 7.6 |
| Normal prostate epithelium | 13.1 ± 4.1 | 10.0 ± 2.6 | 14.3 ± 1.9 |

[1]Mean percent specific lysis (+S.D.) at 1000 pfu/cell.
[2]Mean percent specific lysis (–S.D.) with 1 μg ml soluble TRAIL.

Figure 3B:
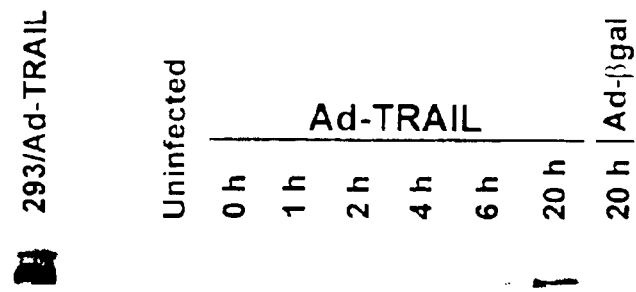

Analysis of TRAIL protein production by Western blot revealed detectable levels in PC-3 cell lysates by 1 hour post-infection, with levels increasing over the entire time course (FIG. 3B). In contrast, lysates from uninfected PC-3 cells or PC-3 cells examined 20 hours after Ad5-βgal infection had no detectable TRAIL protein present. Thus, these results demonstrate that tumor cells infected with Ad5-TRAIL produce TRAIL protein that, presumably, leads to their death.

Example 4

Ad5-TRAIL Infection Induces Apoptosis in Tumor Cell Targets

Figure 4A:
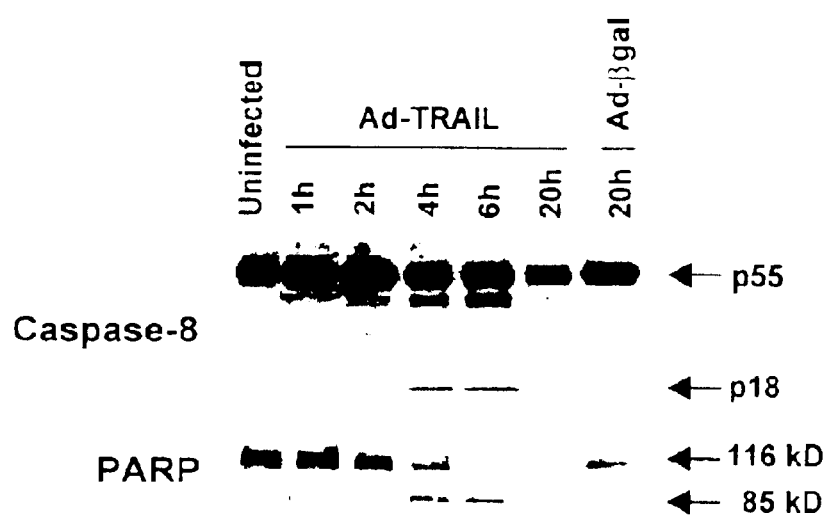
FIG. 4. Ad5-TRAIL-infected PC-3 cells undergo apoptotic cell death. (A). Kinetics of caspase-8 and PARP cleavage following Ad5-TRAIL infection. 24-infection and caspase-8 and PARP cleavage was determined by Western blot analysis. Caspase-8 activation yields an 18 kD active subunit from the 55 kD inactive form. Cleavage of PARP from 116 kD to 85 kD occurs during apoptotic cell death. For comparison, lysates from uninfected or Ad5-βgal-infected PC-3 cells were also examined. (B). Inhibition of Ad5-TRAIL-induced apoptosis by z-VAD-fmk. Microtiter plates were seeded with $2 \times 10^4$ cells/well and allowed to adhere for at least 6 hours. Ad5-TRAIL infection (1000 pfu/cell) was done in the presence of either z-VAD-fmk (20 µM) or DMSO, which were also added to the medium after infection. Cells infected with Ad5-TRAIL or Ad5-βgal in medium alone served as controls. Cell viability was determined after 20 hours by crystal violet staining. Each value represents the mean of 3 wells. For clarity, standard deviation bars were omitted from the graph, but were less than 5% for all data points. Experiments were performed at least three separate times with similar results. (C). Ad5-TRAIL-infected cells externalize phosphatidylserine (PS). PC-3 cells were infected with Ad5-TRAIL or Ad5-βgal (1000 pfu/cell) for 4 hours, and then cultured for 6 hours in complete medium. Cells were then stained with FITC-annexin V and analyzed by flow cytometry. Cells treated with recombinant, soluble TRAIL (100 ng/ml) served as a positive control. The percent of FITC-annexin V positive tumor cells is indicated for each condition. Histograms represent $10^4$ gated tumor cells.
Figure 4B:
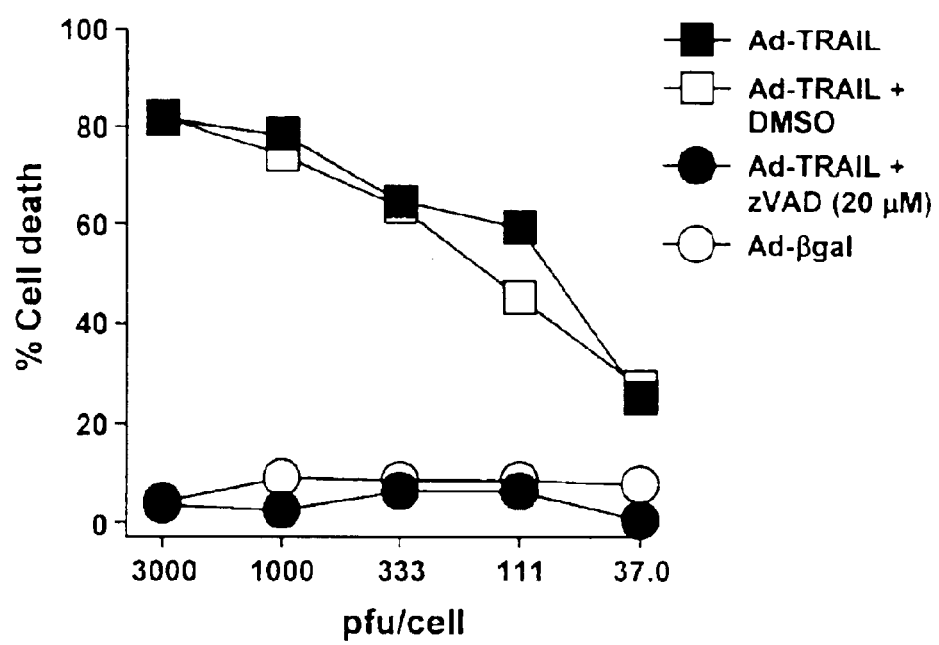

Although crystal violet staining of the tumor cells infected with the adenoviral vectors or treated with recombinant TRAIL as presented in FIG. 3 indicates the amount of cell death, it does not discriminate between apoptotic and necrotic cell death. Previous reports have demonstrated that TRAIL-induced cell death occurs through an apoptotic mechanism characterized by the activation of a cascade of intracellular proteases, or caspases, and the cleavage of numerous intracellular proteins (9,10,14,34–36). To confirm that the tumor cell death following Ad5-TRAIL infection was mediated through an apoptotic mechanism, caspase activation and cellular protein cleavage were examined. Thus, PC-3 cells were infected with Ad5-TRAIL for 4 hours, cell lysates were prepared at various times after infection, and the cellular proteins were separated by SDS-PAGE for Western blot analysis of caspase-8 activation and poly (ADP-ribose) polymerase (PARP) cleavage. Activation of caspase-8 occurred within 2 hours after infection, while PARP cleavage took place by 4 hours after infection (FIG. 4A). By 20 hours after infection, the levels of the active p18 subunit of caspase-8 and 85-kDa fragment of PARP had dropped below the level of detection, due to extensive apoptotic destruction. To further demonstrate the importance of caspase activation in the death of Ad5-TRAIL-infected cells, the caspase inhibitor z-VAD-fmk (carbobenzyloxy-Val-Ala-Asp (OMe) fluoromethyl ketone) was added to the culture medium throughout the assay. z-VAD-fmk completely inhibited PC-3 cell death.

Figure 4C:
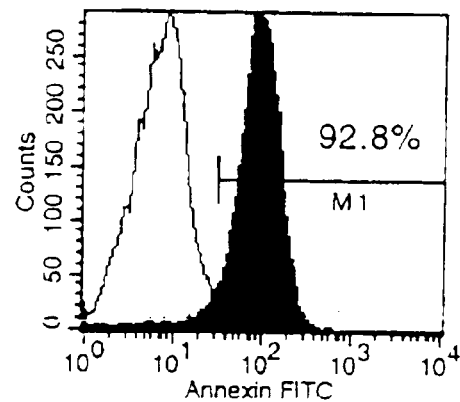
Figure 4C:
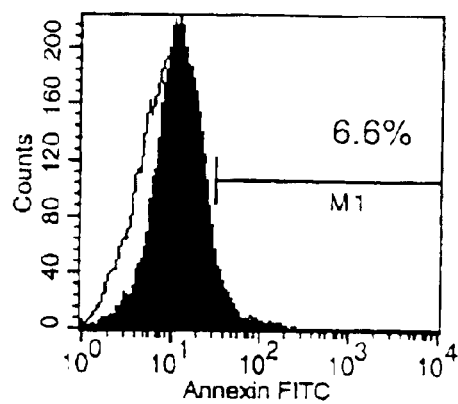
Figure 4C:
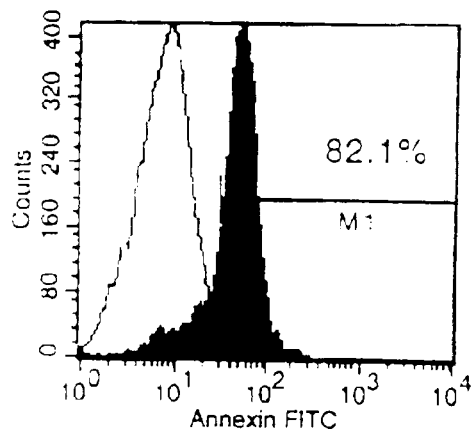

A second critical event that takes place during apoptosis is the alteration in plasma membrane composition that appears to serve as a signal for phagocytes to recognize and engulf the apoptotic cells before membrane integrity is compromised. It has been suggested that phosphatidylserine, a phospholipid component of the inner leaflet of the cell membrane that appears in the outer leaflet during apoptosis, serves as the marker for phagocytosis (37,38). Annexin V has been shown to preferentially bind to phosphatidylserine (39,40), and can be used to detect the expression of phosphatidylserine on apoptotic cells (29,30). Thus, PC-3 cells infected with Ad5-βgal or Ad5-TRAIL were analyzed for annexin V binding. Upon staining the PC-3 cells 6 hours after infection or incubation with soluble hTRAIL (100 ng/ml), only those cells infected with Ad5-TRAIL or incubated with soluble hTRAIL were positive for FITC-annexin V binding (FIG. 4C), providing further evidence that the death of the Ad5-TRAIL-infected tumor cells was through an apoptotic mechanism. Morphological changes, such as membrane blebbing and the release of apoptotic bodies, were also observed in cells infected with Ad5-TRAIL using light microscopy.

Example 5

Figure 5A:
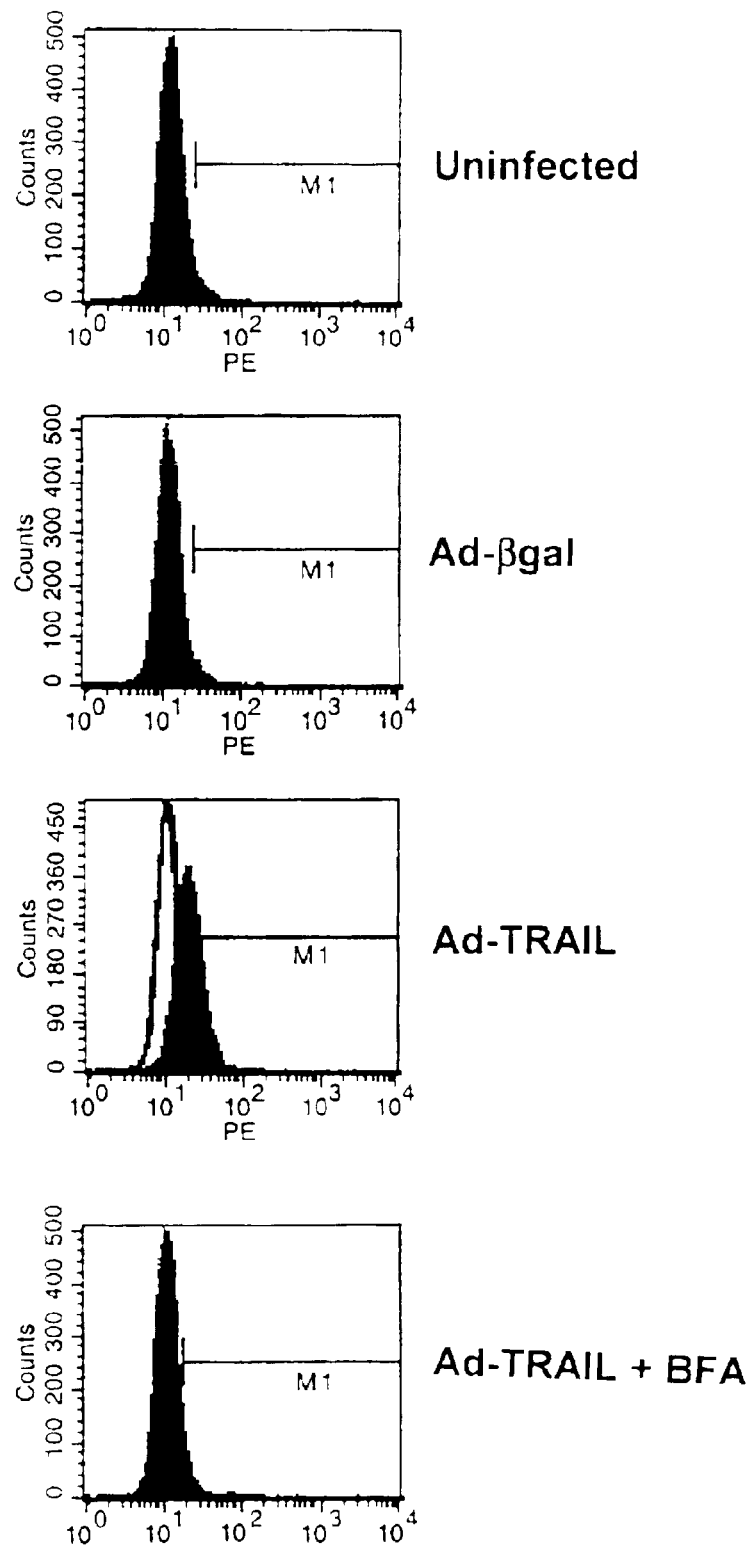
FIG. 5. TRAIL expression following Ad5-TRAIL infection. (A) Flow cytometric analysis of TRAIL protein expression on WM 164 cells. WM 164 cells were infected with Ad5-βgal or Ad5-TRAIL (1000 pfu/cell) for 4 hours, and then analyzed for TRAIL expression after 12 hours. Some of the Ad5-TRAIL-infected cells were also cultured in the presence of Brefeldin A (BFA; 5 µg/ml) during and after infection. Open histograms represent staining by the isotype control, whereas filled histograms represent staining by M181 (anti-TRAIL mAb). Histograms represent $10^4$ gated cells in all conditions. (B). Brefeldin A treatment does not lysates were prepared at the indicated times after infection, and TRAIL protein levels were determined by Western blot analysis. A lysate of Ad5-TRAIL-infected 293 cells was used as a positive control.
Figure 5B:
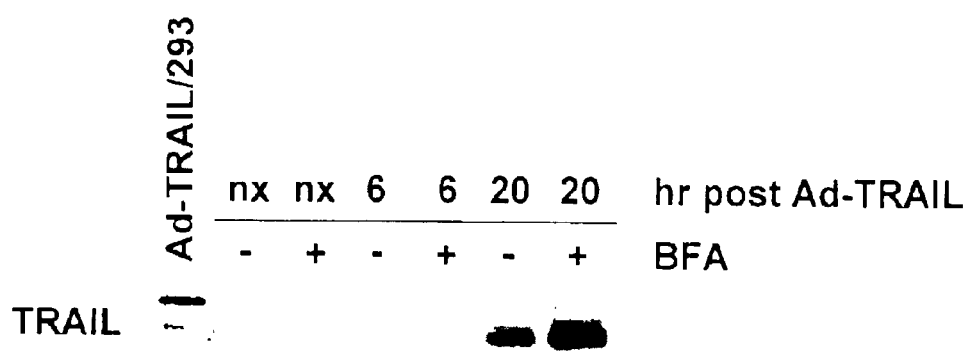

Ad5-TRAIL-induced Death can be Inhibited with Brefeldin A, but not TRAIL Receptor:Fc The results obtained thus far demonstrated that Ad5-TRAIL infection leads to TRAIL protein production and the subsequent induction of apoptotic cell death. However, it was important to also demonstrate the cell death to be a TRAIL-dependent phenomenon with the expression of TRAIL on the surface of the infected cells. Thus, the TRAIL-resistant (both soluble TRAIL (recombinant soluble hTRAIL was purchased from PeproTech and used at the indicated concentrations) and Ad5-TRAIL) human melanoma WM164 was infected with Ad5-βgal or Ad5-TRAIL as in previous experiments, and then analyzed for TRAIL expression by flow cytometry after 8 hours. TRAIL-resistant WM 164 cells were used because the increased as the cells became apoptotic. Whereas no TRAIL was detectable on uninfected or Ad5-βgal-infected WM 164 cells, those cells infected with Ad5-TRAIL did express TRAIL on the cell surface (FIG. 5A). Interestingly, treatment of the Ad5-TRAIL-infected WM 164 cells with Brefeldin A (BFA) resulted in the inhibition of TRAIL expression at the cell surface. BFA blocks the anterograde migration of proteins through the Golgi complex, and thus prevents their expression on the cell surface. The BFA treatment did not, however, inhibit the production of TRAIL protein as both treated and untreated Ad5-TRAIL-infected WM 164 cell lysates contained TRAIL protein as determined by Western blotting (FIG. 5B).

Since TRAIL must bind to TRAIL-R1 or -R2 (the death domain, death-inducing TRAIL receptors) to initiate the apoptotic process, it was predicted that disruption of this interaction would protect the TRAIL-sensitive tumor cells from Ad5-TRAIL-induced death. To test this, PC-3 cells were infected with Ad5-TRAIL and then cultured for 20 hours in medium alone, or medium containing the recombinant soluble receptors for TRAIL (TRAIL-R2:Fc, Ref. 14) or Fas (Fas:Fc). Surprisingly, TRAIL-R2:Fc did not inhibit cell death in the Ad5-TRAIL-infected PC-3 cells (FIG. 6A) at concentrations that completely inhibited cell death induced by soluble TRAIL. It was reasoned that since the PC-3 cells are adherent, nonpolarized cells TRAIL could be expressed on surfaces that were inaccessible to TRAIL-R2:Fc, but still able to engage the TRAIL-R1 or -R2 expressed there. Seeing that BFA could inhibit the expression of TRAIL (FIG. 5A), the same experiment was tried but in the presence of BFA or its vehicle EtOH. In this setting, the addition of BFA was able to block the cell death resulting from Ad5-TRAIL infection, whereas EtOH did not (FIG. 6B). This inhibition by BFA did not interfere with the signaling mechanism of TRAIL-R1/R2 as BFA-treated PC-3 cells were as sensitive to soluble TRAIL-induced death as those cultured without BFA (data not shown).

Further support for TRAIL-mediated killing following Ad5-TRAIL infection Ad5-TRAIL for 4 hours, incubated in complete medium for 12 hours, washed, and resuspended in complete medium. PC-3 tumor cells were labeled with 100 $\mu$Ci of $^{51}$Cr for 1 hour at 37 C, washed three times, and resuspended in complete medium. To determine TRAIL-induced death. $^{51}$Cr-labeled tumor cells ($10^4$/well) were incubated with varying numbers of Ad5-TRAIL/WM 164 effector cells for 8 hours. As a positive control, soluble TRAIL was added to the target cells at the indicated concentrations. In some cultures, TRAIL-R2:Fc or Fas:Fc (20 $\mu$g/ml) were added to the Ad5-TRAIL/WM 164 effector cells 15 minutes prior to adding tumor cell targets. Assays were performed in round-bottom 96-well plates and the percent specific lysis was calculated as: 100× (experimental c.p.m.—spontaneous c.p.m.)/(total c.p.m.—spontaneous c.p.m.). Spontaneous and total release were determined in the presence of either medium alone or 1% NP-40, respectively. The presence of TRAIL-R2:Fc or Fas:Fc during the assay had no effect on the level of spontaneous release of $^{51}$Cr by the target cells.

Figure 6:
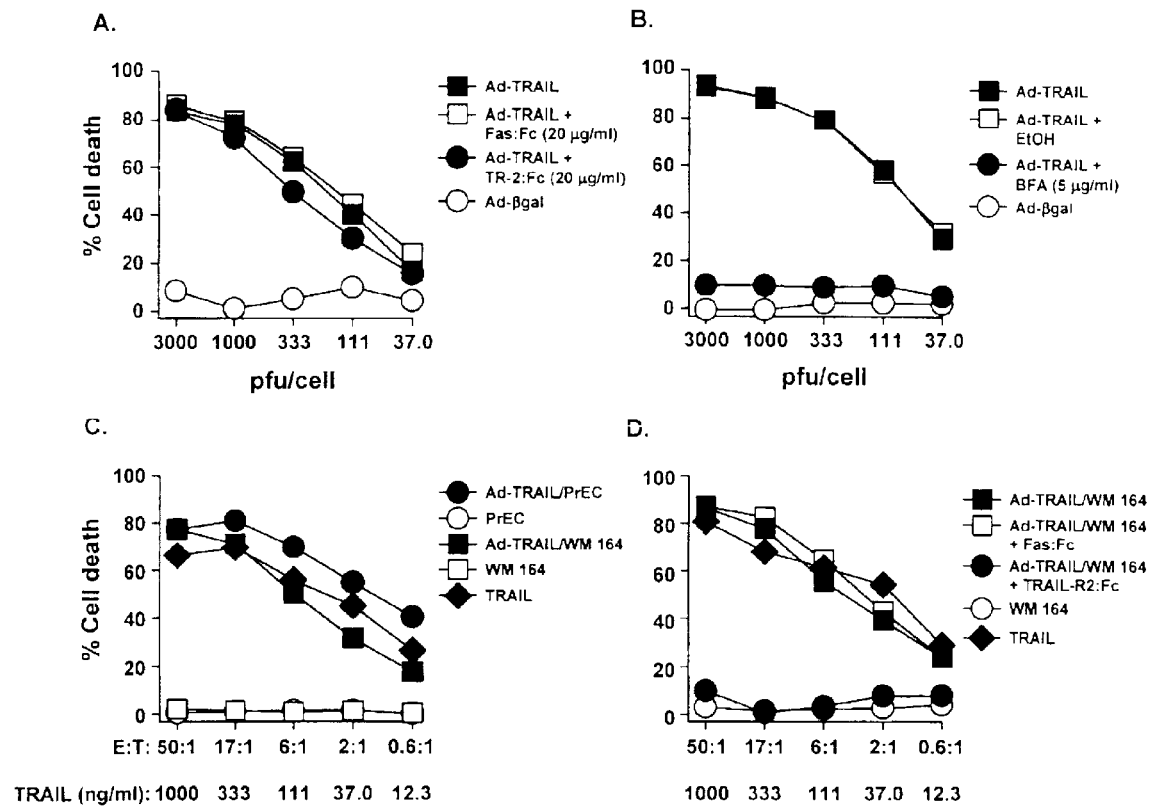
FIG. 6. Tumor cell death after Ad5-TRAIL infection can be inhibited by Brefeldin A, but not TRAIL receptor:Fc. Microtiter plates were seeded with $2 \times 10^4$ PC-3 cells/well and allowed to adhere for at least 6 hours before infection with Ad5-TRAIL alone or in the presence of (A) TRAIL-R2:Fc(TR-2:Fc; 20 µg/ml), (A) Fas:Fc (20 µg/ml), (B) Brefeldin A (BFA; 5 µg/ml), (B) EtOH, or Ad5-βgal alone at the indicated number of pfu/cell for 4 hours. Cells were washed with PBS, and then incubated with medium alone, medium containing TR-2:Fc, Fas:Fc, BFA, or EtOH, or medium containing recombinant TRAIL (TRAIL) at the indicated concentrations. Cell viability was determined after 20 hours by crystal violet staining. (C). PrEC or WM 164 cells were infected with Ad5-TRAIL (1000 pfu/cell) for 4 hours, incubated for 12 hours, and then cultured for 8 hours with $^{51}$Cr-labeled PC-3 target cells at the indicated effector-target cell ratios. Soluble TRAIL or uninfected PrEC or WM 164 cells were used as positive and negative controls, respectively, and added to target cells as indicated. (D) Inclusion of the fusion protein TRAIL-R2:Fc (20 µg/ml) to Ad5-TRAIL-infected WM 164 cells inhibited killing of PC-3 target cells, while addition of Fas:Fc (20 µg/ml) did not. Each value represents the mean of three wells. For clarity, S.D. bars were omitted, but were <5% for all data points. Similar results were observed in three independent experiments.

Whereas uninfected PrEC or WM 164 demonstrated no cytolytic activity against the PC-3 target cells, the Ad5-TRAIL-infected cells displayed comparable activity to soluble TRAIL (FIG. 6C). This activity was TRAIL-specific, as inclusion of soluble TRAIL-R2: Fc, but not Fas:Fc, to the Ad5-TRAIL-infected WM 164 cells blocked target cell lysis (FIG. 6D). Similar results were also obtained with PrEC (data not shown). Collectively, the results presented in FIGS. 5 and 6 demonstrate that the apoptotic death following Ad5-TRAIL infection results from TRAIL expression on the cell surface where it binds to either TRAIL-R1 or -R2.

Example 6

Analysis of Adenoviral Transgene Expression Following Intratumoral Injection

CB.17 SCID mice were pretreated 24 hours before tumor challenge with a single injection (100 $\mu$l, intraperitoneally) of purified anti-asialo GM-1 antibody (Wako Chemicals, Richmond, Va.). Mice were challenged with either the human grow until they were at least 25 mm$^2$ before the adenoviral vectors recombinant for the reporter genes luciferase (Ad2-luc) or β-galactosidase (Ad5- gal) were injected at a concentration of 3×10$^7$ plaque forming units (pfu)/ml in PBS (phosphate buffered saline) alone or with Gelfoam* (30 mg/ml; Pharmacia and Upjohn, Kalamazoo, Mich.). Gelfoam* is an absorbable gelatin sponge prepared from purified pork skin gelatin and is commonly used as a hemostatic agent. Injection volume was 100 ml, making the final concentration 3×10$^6$ pfu/injection. Tumors were harvested for reporter gene assays at various times after injection.

The luciferase assay or β-galactosidase was performed using a commercial luciferase (Promega Corp., Madison, Wis.) or β-galactosidase (Tropix, Bedford, Mass.) assay kit after homogenizing each tumor. Samples were analyzed on a Monolight 2010 Luminometer (Analytical Luminescence Laboratory, Ann Arbor, Mich.).

Example 7

Inhibition of Tumor Growth with Ad5-TRAIL

CB.17 SCID mice were pretreated 24 hours before tumor challenge with a single injection (100 $\mu$l, intraperitoneally)

of purified anti-asialo GM-1 antibody. Mice were challenged with the human bladder cancer cell line RT-4 ($5 \times 10^6$ cells/site) by subcutaneous injection. Mice were then treated with either PBS alone, Ad5-TRAIL in PBS, Ad5-TRAIL with matrix, Ad5-βgal in PBS, or Ad5-βgal with matrix ($10^9$ pfu/injection) 24 hours later. Tumor size was measured weekly.

The Ad5-TRAIL treatment is also useful for the treatment of established tumors. Tumors are implanted and then the Ad5-TRAIL treatment is begun days later (Day 0, implant; Day 1, 5, 7, 10, 14, 21 inject Ad5-TRAIL). Tumor size is measured before and after treatment.

The Ad5-TRAIL treatment can be administered as multiple Ad5-TRAIL injections as opposed to a single injection. Experimental groups are set up as above, but with groups receiving multiple Ad5-TRAIL injections at regular intervals. described with reference to various specific and preferred embodiments and techniques. However, it should be understood that many variations and modifications may be made while remaining within the scope of the invention.

REFERENCES

1. Armitage, R. J. 1994. Tumor necrosis factor receptor superfamily members and their ligands. *Curr. Opin. Immunol.* 6:407.
2. Cosman, D. 1994. A family of ligands for the TNF receptor superfamily. *Stem Cells* 12:440.
3. Schulze-Osthoff, K., D. Ferrari, M. Los, S. Wesselborg, and M. E. Peter. 1998. Apoptosis signaling by death receptors. *Eur. J. Biochem.* 254:439.
4. Cerami, A., and B. Beutler. 1988. The role of cachectin/TNF in endotoxic shock and cachexia. *Immunol. Today* 9:28.
5. Zheng, L. X., G. Fisher, R. E. Miller, J. Peschon, D. H. Lynch, and M. J. Lenardo. 1995. Induction of apoptosis in mature T cells by tumor necrosis factor. *Nature* 377:348.
6. Alderson, M. R., T. W. Tough, T. Davis-Smith, S. Braddy, B. Falk, K. A. Schooley, R. G. Goodwin, C. A. Smith, F. Ramsdell, and D. H. Lynch. 1995. Fas ligand mediates activation-induced cell death in human T lymphocytes. *J. Exp. Med.* 181:71.
7. Griffith, T. S., T. Brunner, S. M. Fletcher, D. R. Green, and T. A. Ferguson. 1995. Fas ligand-induced apoptosis as a mechanism of immune privilege. *Science* 270:1189.
8. Hahne, M., D. Rimoldi, M. Schroter, P. Romero, M. Schreier, L. E. French, P. Schneider, T. Bornand, A. Fontana, D. Lienard, J.-C. Cerottini, and J. Tschopp. 1996. Melanoma cell expression of Fas (Apo-1/CD95) ligand: implications for tumor immune escape. *Science* 274:1363.
9. Wiley, S. R., K. Schooley, P. J. Smolak, W. S. Din, C.-P. Huang, J. K. Nicholl, G. R. Sutherland, T. Davis Smith, C. Rauch, C. A. Smith, and R. G. Goodwin. 1995. Identification and characterization of a new member of the TNF family that induces apoptosis. *Immunity* 3:673.
10. Pitti, R. M., S. A. Marsters, S. Ruppert, C. J. Donahue, A. Moore, and A. Ashkenazi. 1996. Induction of apoptosis by Apo-2 ligand, a new member of the tumor necrosis factor cytokine family. *J. Biol. Chem.* 271:12687.
11. Pan, G., K. O'Rourke, A. M. Chinnaiyan, R. Gentz, R. Ebner, J. Ni, and V. M. Dixit. 1997. The receptor for the cytotoxic ligand TRAIL. *Science* 276:111.
12. Pan, G., J. Ni, Y.-F. Wei, G.-I. Yu, R. Gentz, and V. M. Dixit. 1997. An antagonist decoy receptor and a death domain-containing receptor for TRAIL. *Science* 277:815.
13. Sheridan, J. P., S. A. Marsters, P. M. Pitti, A. Gurney, M. Skubatch, D. Baldwin, L. Ramakrishnan, C. L. Gray, K. Baker, W. I. Wood, A. D. Goddard, P. Godowski, and A. Ashkenazi. 1997. Control of TRAIL induced apoptosis by a family of signaling and decoy receptors. *Science* 277:818.
14. Walczak, H., M. A. Degli-Esposti, R. S. Johnson, P. J. Smolak, J. Y. Waugh, N. Boiani, M. S. Timour, M. J. Gerhart, K. A. Schooley, C. A. Smith, R. G. Goodwin, and C. T. Rauch. 1997. TRAIL-R2: a novel apoptosis-mediating
15. MacFarlane, M., M. Ahmad, S. M. Srinivasula, T. Fernandes-Alnemri, G. M. Cohen, and E. S. Alnemri. 1997. Identification and molecular cloning of two novel receptors for the cytotoxic ligand TRAIL. *J. Biol. Chem.* 272:25417.
16. Degli-Esposti, M. A., P. J. Smolak, H. Walczak, J. Waugh, C.-P. Huang, R. F. DuBose, R. G. Goodwin, and C. A. Smith. 1997. Cloning and characterization of TRAIL-R3, a novel member of the emerging TRAIL receptor family. *J. Exp. Med.* 186:1165.
17. Degli-Esposti, M. A., W. C. Dougall, P. J. Smolak, J. Y. Waugh, C. A. Smith, and R. G. Goodwin. 1997. The novel receptor TRAIL-R4 induces NFxB and protects against TRAIL-mediated apoptosis, yet retains an incomplete death domain. *Immunity* 7:813.
18. Marsters, S. A., J. P. Sheridan, R. M. Pitti, A. Huang, M. Skubatch, D. Baldwin, J. Yuan, A. Gurney, A. D. Goddard, P. Godowski, and A. Ashkenazi. 1997. A novel receptor for Apo2L/TRAIL contains a truncated death domain. *Curr. Biol.* 7:1003.
19. Pan, G., J. Ni, G. Yu, Y.-F. Wei, and V. M. Dixit. 1998. TRUNDD, a new member of the TRAIL receptor family that antagonizes TRAIL signaling. *FEBS Lett.* 424:41.
20. Walczak, H., R. E. Miller, B. Gliniak, K. Ariail, T. S. Griffith, M. Kubin, W. Chin, J. Jones, A. Woodward, T. Le, C. Smith, P. Smolak, R. G. Goodwin, C. T. Rauch, J. C. L. Schuh, and D. H. Lynch. 1999. Tumoricidal activity of TRAIL in vivo. *Nat. Med.* 5:157.
21. Ashkenazi, A., R. C. Pai, S. Fong, S. Leung, D. A. Lawrence, S. A. Marsters, C. Blackie, L. Chang, A. E. McMurtrey, A. Hebert, L. DeForge, I. L. Koumenis, D. Lewis, L. Harris, J. Bussiere, H.Koeppen, Z. Shahrokh, and R. H. Schwall. 1999. Safety and antitumor activity of recombinant soluble Apo2 ligand. *J. Clin. Invest.* 104:155.
22. Gliniak, B., and T. Le. 1999. Tumor necrosis factor-related apoptosis-inducing ligand's antitumor activity in vivo is enhanced by the chemotherapeutic agent CPT-11. *Cancer Res.* 59:6153.
23. Schneider, P., N. Holler, J. L. Bodmer, M. Hahne, K. Frei, A. Fontana, and J. Tschopp. 1998. Conversion of membrane-bound Fas (CD95) ligand to its soluble form is associated with downregulation of its proapoptotic activity and loss of liver toxicity. *J. Exp. Med.* 187:1205.
24. Ogasawara, J., F. R. Watanabe, M. Adachi, A. Matsuzawa, T. Kasugai, Y. Kitamura, N. Itoh, T. Suda, and S. Nagata. 1993. Lethal effect of the anti-Fas antibody in mice. *Nature* 364:806.
25. Kayagaki, N., N. Yamaguchi, M. Nakayama, A. Kawasaki, H. Akiba, K. Okumura, and H. Yagita. 1999. Involvement of TNF-related apoptosis-inducing ligand in human CD4$^+$ T cell-mediated cytotoxicity. *J. Immunol.* 162:2639.
26. Ooboshi, H., Y. Chu, C. D. Rios, F. M. Faraci, B. L. Davidson, and D. D.
27. Jones, N., and T. Shenk. 1979. Isolation of adenovirus type 5 host range deletion mutants defective for transformation of rat embryo cells. *Cell* 17:683.

28. Flick, D. A., and G. E. Gifford. 1994. Comparison of in vitro cell cytotoxic assays for tumor necrosis factor. *J. Immunol. Meth.* 68:167.
29. Koopman, G., C. P. M. Reutelingsperger, G. A. M. Kuijten, R. M. J. Keehnen, S. T. Pals, and M. H. J. van Oers. 1994. Annexin V for flow cytometric detection of phosphatidylserine expression on B cells undergoing apoptosis. *Blood.* 84:1415.
30. Martin, S. J., C. P. M. Reutelingsperger, A. J. McGahon, J. A. Rader, R. C. A. A. van Schie, D. M. LaFace, and D. R. Green. 1995. Early redistribution of plasma membrane phosphatidylserine is a general feature of apoptosis regardless of the initiating stimulus: Inhibition by overexpression of Bcl-2 and Abl. *J. Exp. Med.* 182:1545.
31. Wickham, T. J., P. Mathias, D. A. Cheresh, and G. R. Nemerow. 1993. Integrins $\alpha_v\beta_1$ and $\alpha_v\beta_5$ promote adenovirus internalization but not virus attachment. *Cell* 23:309.
32. Bergelson, J. M., J. A. Cunningham, G. Droguett, E. A. Kurt-Jones, A. Krithivas, J. S. Hong, M. S. Horwitz, R. L. Crowell, and R. W. Finberg. 1997. Isolation of a common receptor for coxsackie B viruses and adenoviruses 2 and 5. *Science* 275:1320.
33. Tomko, R. P., R. Xu, and L. Philipson. 1997. HCAR and MCAR: The human and mouse cellular receptors for subgroup C adenoviruses and group B coxsackieviruses. *Proc. Natl. Acad. Sci. USA.* 94:3352.
34. Chaudhary, P. M., M. Eby, A. Jasmin, A. Bookwalter, J. Murray, and L. Hood. 1997. Death receptor 5, a new member of the TNFR family, and DR4 induce FADD-dependent apoptosis and activate the NF-κB pathway. *Immunity* 7:821.
35. Schneider, P., M. Thome, K. Burns, J. L. Bodmer, K. Hofmann, T. Kataoka, N. Holler, and J. Tschopp. 1997. TRAIL receptors 1(DR4) and 2 (DR5) signal FADD-dependent apoptosis and activate NF-κB. *Immunity* 7:831.
36. Griffith, T. S., W. A. Chin, G. C. Jackson, D. H. Lynch, and M. Z. Kubin. 1998. Intracellular regulation of TRAIL-induced apoptosis in human melanoma cells. *J. Immunol.* 161:2833.
37. Fadok, V. A., D. R. Voelker, P. A. Campbell, J. J. Cohen, D. L. Bratton, and P. M. Henson. 1992. Exposure of phosphatidylserine on the surface of apoptotic lymphocytes triggers specific recognition and removal by macrophages. *J. Immunol.* 148:2207.
38. Fadok, V. A., J. S. Savill, C. Haslett, D. L. Bratton, D. E. Doherty, P. A. Campbell, and P. M. Henson. 1992. Different populations of macrophages use either the vitronectin receptor or the phosphatidylserine receptor to recognize and remove apoptotic cells. *J. Immunol.* 149:4029.
39. Thiagarajan, P., and J. F. Tait. 1990. Binding of annexin V placental
40. Raynal, P., and H. B. Pollard. 1994. Annexins: the problem of assessing the biological role for a gene family of multifinctional clacium and phospholipid-binding proteins. *Biochim. Biophys. Acta.* 1197:63.
41. Willimsky, G., and T. Blankenstein. 2000. Interleukin-7/B7.1-encoding adenoviruses induce rejection of transplanted by not nontransplanted tumors. *Cancer Res* 60:685.
42. Lu, W., I. J. Fidler, and Z. Dong. 1999. Eradication of primary murine fibrosacromas and induction of systemic immunity by adenovirus-mediated interferon beta gene therapy. *Cancer Res.* 59:5202.
43. Stewart, A. K., N. J. Lassam, I. C. Qquirt, D. J. Bailey, L. E. Rotstein, M. Krajden, S. Dessureault, S. Gallinger, D. Cappe, Y. Wan, C. L. Addison, R. C. Moen, J. Gauldie, and F. L. Craham. 1999. Adenovector-mediated gene delivery of interleukin-2 in metastatic breast cancer and melanoma: Results of a phase 1 clinical trial. *Gene Ther.* 6:350.
44. Hirschowitz, E. A., H. A. Naama, D. Evoy, M. D. Lieberman, J. Daly, and R. G. Crystal. 1999. Regional treatment of hepatic micrometastasis by adenovirus vector-mediated delivery of interleukin-2 and interleukin-12 cDNAs to the hepatic parenchyma. *Cancer Gene Ther.* 6:491.
45. Nasu, Y., C. H. Bangma, G. W. Hull, H. M. Lee, J. Hu, J. Wang, M. A. McCurdy, S. Shimura, G. Yang, T. L. Timme, and T. C. Thompson. 1999. Adenovirus-mediated interleukin-12 gene therapy for prostate cancer: Suppression of orthotopic tumor growth and pre-established lung metastases in an orthotopic model. *Gene Ther.* 6:338.
46. Mazzolini, G., C. Quin, X. Xie, Y. Sun, J. J. Lasarte, M. Drozdzik, and J. Prieto. 1999. Regression of colon cancer and induction of antitumor immunity by intratumoral injection of adenovirus expressing interleukin-12. *Cancer Gene Ther.* 6:514.
47. Atkinson, G., and S. J. Hall. 1999. Prodrug activation gene therapy and external beam irradiation in the treatment of prostate cancer. *Urology* 54:1098.
48. Xie, Y., J. D. Gilbert, J. H. Kim, and S. O. Freytag. 1999. Efficacy of adenovirus-mediated CD/5-FC and HSV-1 thymidinekinase/ganciclovir suicide gene therapies concomitant with p53 gene therapy. *Clin. Cancer Res.* 5:4224.
49. Arai, H., D. Gordon, E. G. Nabel, and G. J. Nabel. 1997. Gene transfer of Fas ligand induces tumor regression in vivo. *Proc. Natl. Acad. Sci. USA.* 94:13862.
50. Ambar, B. B., K. Frei, U. Malipiero, A. E. Morelli, M. G. Castro, R. P. Lowerstein, and A. Fontana. 1999. Treatment of experimental glioma by administration of adenoviral vectors expressing Fas ligand. *Hum. Gene Ther.* 10:1641.
51. Hedlund, T. E., S. J. Meech, S. Srikanth, A. S. Kraft, G. J. Miller, J. B. Schaack, and R. C. Duke. 1999. Adenovirus-mediated expression of Fas ligand induces apoptosis of human prostate cancer cells. *Cell Death Diff.* 6:175.
53. Innler, M., M. Thome, M. Hahne, P. Schneider, K. Hofmann, V. Steiner, J. L. Bodmer, M. Schroter, K. Burns, C. Mattmann, D. Rimoldi, L. E. French, and J. Tschopp. 1997. Inhibition of death receptor signals by cellular FLIP. *Nature* 388:190.
54. Leverlcus, M., M. Neumann, T. Mengling, C. T. Rauch, E.-B. Brocker, P. H. Krammer, and H. Walczak. 2000. Regulation of tumor necrosis factor-related apoptosis-inducing ligand sensitivity in primary and transformed human keratinocytes. *Cancer Res.* 60:553.
55. Albert, M. L., B. Sauter, and N. Bhardwaj. 1998. Dendritic cells acquire antigen from apoptotic cells and induce class I-restricted CTLs. *Nature* 392:86.
56. Albert, M. L., S. F. A. Pearce, L. M. Francisco, B. Sauter, P. Roy, R. L. Silverstein, and N. Bhardwaj. 1998. Immature dendritic cells phagocytose apoptotic cells via $\alpha_v\beta_5$ and CD36, and cross-present antigens to cytotoxic T lymphocytes. *J. Exp. Med.* 188:1359.
57. Giovarelli, M., P. Musiani, G. Garotta, R. Ebner, E. Di Carlo, Y. Kim, P. Cappello, L. Rigamonti, P. Bernabei, F. Novelli, A. Modesti, A. Coletti, A. K. Ferriem, P.-L. Lollini, S. Ruben, T. Salcedo, and G. Forni. 1999. A "stealth effect": Adenocarcinoma cells engineered to express TRAIL elude tumor-specific and allogeneic T cell reactions. *J. Immunol.* 163:4886.

58. O'Connell, J., G. C. O'Sullivan, J. K. Collins, and F. Shanahan. 1996. The Fas counterattack: Fas-mediated T cell killing by colon cancer cells expressing Fas ligand. *J. Exp. Med.* 184:1075.
59. O'Connell, J., M. W. Bennett, G. C. O'Sullivan, D. Roche, J. Kelly, J. K. Collins, and F. Shanahan. 1998. Fas ligand expression in primary colon adenocarcinomas: Evidence that the Fas counterattack is a prevalent mechanism of immune evasion in human colon cancer. *J. Pathol.* 186:240.
60. Bennett, M. W., J. O'Connell, G. C. O'Sullivan, C. Brady, D. Roche, J. K. Collins, and F. Shanahan. 1998. The Fas counterattack in vivo: Apoptotic depletion of tumor-infiltrating lymphocytes associated with Fas ligand expression by human esophageal carcinoma. *J. Immunol.* 160:5669.
61. Landis, S. H., T. Murray, S. Bolden, and P. A. Wingo. 1999. Cancer statistics, 1999. *CA Cancer J. Clin.* 49:8.

What is claimed is:

1. A method for inhibiting tumor cell growth in a mammal afflicted with a tumor comprising intratumorally injecting a replication-deficient adenovirus, adeno-associated virus, herpesvirus, lentivirus, retrovirus, or vaccinia virus vector comprising a DNA expression cassette comprising a promoter operably linked to a DNA sequence encoding human or mouse tumor necrosis factor (TNF)-related apoptosis-inducing ligand (TRAIL) including the transmembrane region such that the promoter drives transcription of the DNA sequence encoding TRAIL, and wherein the cell-surface expression of TRAIL on live normal and tumor cells results in tumor cell death.

2. The method of claim 1, wherein the vector is a non-replicative viral vector.

3. The method of claim 2, wherein the vector is an adenoviral vector.

4. The method of claim 1, wherein the TRAIL is human TRAIL.

5. The method of claim 1, wherein the promoter is a cytomegalovirus promoter, a Rouse Sarcoma Virus promoter, or a tissue-specific promoter.

6. The method of claim 5, wherein the promoter is a cytomegalovirus promoter.

7. The method of claim 1, wherein the expression cassette further comprises a regulatory element.

8. The method of claim 7, wherein the regulatory element is an enhancer, regulator of TRAIL expression, or regulator controlling viral replication.

9. The method of claim 1, wherein the tumor is a solid tumor.

10. The method of claim 9, wherein the tumor is cancerous.

11. The method of claim 9, wherein the solid tumor is a lung tumor, a melanoma, a mesothelioma, a mediastinum tumor, esophagal tumor, stomach tumor, pancreal tumor, renal tumor, liver tumor, hepatobiliary system tumor, small intestine tumor, colon tumor, rectum tumor, anal tumor, kidney tumor, ureter tumor, bladder tumor, prostate tumor, urethral tumor, testicular tumor, gynecological organ tumor, ovarian tumor, breast tumor, endocrine system tumor, or central nervous system tumor.

12. The method of claim 1, wherein the vector is administered in combination with a pharmaceutically acceptable carrier.

13. The method of claim 12, wherein the pharmaceutically acceptable carrier is a solution.

14. The method of claim 12, wherein the pharmaceutically acceptable carrier is a slurry or matrix.

15. The method of claim 12, wherein the pharmaceutically acceptable carrier is in a matrix comprising an absorbable hemostatic agent.

16. The method of claim 12, wherein the carrier further comprises an immune enhancing agent.

17. The method of claim 16, wherein the immune enhancing agent is a cytokine.

18. The method of claim 12, wherein the solution further comprises an agent that enhances gene delivery or expression.

19. The method of claim 1, wherein the mammal is a human.

20. The method of claim 1, further comprising administering a chemotherapeutic agent, radiotherapeutic agent, or an immune potentiating gene or protein.

21. A method for causing tumor regression in a mammal afflicted with a tumor comprising intratumorally administering to a TRAIL-sensitive tumor cell a replication-deficient adenovirus, adeno-associated virus, herpesvirus, lentivirus, retrovirus, or vaccinia virus vector comprising DNA encoding human or mouse TRAIL including the transmembrane region, wherein the cell-surface expression of TRAIL on live normal and tumor cells results in tumor regression.

22. A method of eliminating tumor cells from a mammal afflicted with a tumor comprising intratumorally administering to a TRAIL-sensitive tumor cell a replication-deficient adenovirus, adeno-associated virus, herpesvirus, lentivirus, retrovirus, or vaccinia virus vector comprising DNA encoding human or mouse TRAIL including the transmembrane region, wherein the cell-surface expression of TRAIL on live normal and tumor cells results in tumor elimination.

23. A method for causing tumor regression in a mammal afflicted with a tumor comprising intratumorally administering to a TRAIL-sensitive tumor cell a replication-deficient adenovirus vector comprising DNA encoding human or mouse TRAIL including the transmembrane region, wherein the cell-surface expression of TRAIL on live normal and tumor cells results in tumor regression.

24. A method for causing tumor regression in a mammal afflicted with a tumor comprising intratumorally administering to a TRAIL-sensitive tumor cell a replication-deficient adenovirus, adeno-associated virus, herpesvirus, or retrovirus vector comprising DNA encoding human or mouse TRAIL including the transmembrane region, wherein the cell-surface expression of TRAIL on live normal and tumor cells results in tumor regression.

* * * * *